(12) United States Patent
Malmberg et al.

(10) Patent No.: US 11,471,486 B2
(45) Date of Patent: Oct. 18, 2022

(54) SELECTIVE AND CONTROLLED EXPANSION OF EDUCATED NK CELLS

(71) Applicant: Inven2 AS, Oslo (NO)

(72) Inventors: Karl-Johan Malmberg, Oslo (NO); Vivien Beziat, Huddinge (SE)

(73) Assignee: Inven2 AS, Oslo (NO)

( * ) Notice: Subject to any disclaimer, the term of this patent is extended or adjusted under 35 U.S.C. 154(b) by 669 days.

(21) Appl. No.: 14/425,614

(22) PCT Filed: Sep. 4, 2013

(86) PCT No.: PCT/EP2013/068319
§ 371 (c)(1),
(2) Date: Mar. 3, 2015

(87) PCT Pub. No.: WO2014/037422
PCT Pub. Date: Mar. 13, 2014

(65) Prior Publication Data
US 2015/0224143 A1 Aug. 13, 2015

Related U.S. Application Data

(60) Provisional application No. 61/696,414, filed on Sep. 4, 2012.

(51) Int. Cl.
*C12N 5/0783* (2010.01)
*A61K 35/17* (2015.01)
*A61K 45/06* (2006.01)

(52) U.S. Cl.
CPC .............. *A61K 35/17* (2013.01); *A61K 45/06* (2013.01); *C12N 5/0646* (2013.01); *C12N 2501/23* (2013.01); *C12N 2501/2315* (2013.01); *C12N 2501/50* (2013.01); *C12N 2501/59* (2013.01); *C12N 2501/599* (2013.01)

(58) Field of Classification Search
None
See application file for complete search history.

(56) References Cited

U.S. PATENT DOCUMENTS

2011/0044962 A1  2/2011  Beck

FOREIGN PATENT DOCUMENTS

| WO | WO 99/28748 A2 | 6/1999 |
| WO | WO 2006/050270 A2 | 5/2006 |
| WO | WO 2012/071411 A2 | 5/2012 |

OTHER PUBLICATIONS

Pegram et al (Immunol. Cell Biol. 2011, 89: 216-224).*
Bjorkstrom et al (J. Exp. Med. 2011, 1: 13-21).*
Guma et al (Eur. J. Immunol. 2005, 35: 2071 -2080).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Bakker and Schumacher (Curr. Opin. Immunol. 2005, 17(4): 428-433) (Year: 2005).*
Beziat et al (Blood, Apr. 4, 2013, 121(14): 2678-2688) (Year: 2013).*
Hoare et al (JMB, 2008, 377: 1297-1303) (Year: 2008).*
Braud et al (Nature, 1998, 391: 795-799) (Year: 1998).*
Braud et al (Eur. J. Immunol. 1997, 27: 1164-1169) (Year: 1997).*
Miller et al (J. Immunol. 2003, 171: 1369-1375) (Year: 2003).*
Kremer et al (Stem Cells Intern. 2015, Article ID 346714, pp. 1-12) (Year: 2015).*
Siegers and Lamb (moleculartherapy.org, 2014, 22 (8), 1416-1422) (Year: 2014).*
Merriam-Webster (merriam-webster.com/dictionary/leukocyte, 2021, pp. 1/1-11/11) (Year: 2021).*
Hewitt, E.W. (Immunology, 2003, 110: 163-169) (Year: 2003).*
Beziat, Vivien, et al., "NK cell responses to cytomegalovirus infection lead to stable imprints in the human KIR repertoire and involve activating KIRs", *Blood*, Apr. 4, 2013, vol. 121, No. 14, pp. 2678-2688.
Bjorklund, Andreas T., et al., "NK cells expressing inhibitory KIR for non-self-ligands remain tolerant in HLA-matched sibling stem cell transplantation", *Blood*, Apr. 1, 2010, vol. 115, No. 13, pp. 2686-2694.
Della Chiesa, Mariella, et al., "Phenotypic and functional heterogeneity of human NK cells developing after umbilical cord blood transplantation: a role for human cytomegalovirus?", *Blood*, Jan. 12, 2012, vol. 119, No. 2, pp. 399-410.

(Continued)

*Primary Examiner* — G. R. Ewoldt
*Assistant Examiner* — Marianne DiBrino
(74) *Attorney, Agent, or Firm* — Melissa Hunter-Ensor; Evelyn Kwon; Greenberg Traurig, LLP

(57) ABSTRACT

The present invention relates generally to immunotherapy. Disclosed herein are methods for obtaining cytolytic differentiated NKG2A⁻NKG2C⁺ cells with a given KIR specificity and also compositions comprising these cells as well as the use of these cells for therapy. The NK cell expansion methods provided herein also have non-therapeutic uses.

15 Claims, 16 Drawing Sheets

(56) References Cited

OTHER PUBLICATIONS

Guma, Monica, et al., "The CD94/NKG2C killer lectin-like receptor constitutes an alternative activation pathway for a subset of CD8[+] T cells", *Eur. J. Immunol.*, 2005, vol. 35, pp. 2071-2080.

Guma, Monica, et al., "Expansion of CD94/NKG2C[+] NK cells in response to human cytomegalovirus-infected fibroblasts", *Blood*, May 1, 2006, vol. 107, No. 9, pp. 3624-3631.

Igarashi, Takehito, et al., "Enhanced cytotoxicity of allogenic NK cells with killer immunoglobulin-like receptor ligand incompatibility against melanoma and renal cell carcinoma cells", *Blood*, Jul. 1, 2004, vol. 104, No. 1, pp. 170-177.

Koh, L-P, et al., "Haploidentical hematopoietic cell transplantation", *Bone Marrow Transplantation*, 2008, vol. 42, pp. S60-S63.

Leung, Wing, et al., "Determinants of Antileukemia Effects of Allogenic NK Cells[1]", *The Journal of Immunology*, 2004, vol. 172, pp. 644-650.

Lopez-Verges, Sandra, et al., "Expansion of a Unique CD57[+] NKG2C[hi] natural killer cell subset during acute human cytomegalovirus infection", *PNAS*, Sep. 6, 2011, vol. 108, No. 36, pp. 14725-14732.

Miller, Jeffrey S., et al., "Successful adoptive transfer and in vivo exansion of human haploidentical NK cells in patients with cancer", *Blood*, Apr. 15, 2005, vol. 10 5, No. 8, pp. 3051-3057.

Moretta, Lorenzo, et al., "Killer Ig-like receptor-mediated control of natural killer cell alloreactivity in haploidentical hematopoietic stem cell transplantation", *Blood*, Jan. 20, 2011, vol. 117, No. 3, pp. 764-771.

Orr, Mark T., et al., "'Unlicensed' Natural Killer cells dominate the response to cytomegalovirus infection", *Nat. Immunol.*, Apr. 2010, vol. 11, No. 4, pp. 321-327.

Siegler, Uwe, et al., "Good manufacturing practice-compliant cell sorting and large-scale expansion of single KIR-positive alloreactive human natural killer cells for multiple infusions to leukemia patients", *Cytotherapy*, 2010, vol. 12, pp. 750-763.

Stangle, Stefan, et al., "Influence of Hsp70 and HLA-E on the killing of leukemic blasts by cytokine/Hsp70 peptide-activated human natural killer (NK) cells", *Cell Stress and Chaperones*, 2008, vol. 13, No. 2, pp. 221-2230; XP002591918.

Beziat, Vivien, et al., "CMV drives clonal expansion of NKG2C+ NK cells expressing selfspecific KIRs in chronic hepatitis proteins", *European Journal of Immunology*, 2012, vol. 42, No. 2, pp. 447-457; XP009173335.

Andersson, Sandra, et al., "KIR acquisition of probabilities are independent of self-HLA class I ligands and increase with cellular KIR expression", *Blood*, 2009, vol. 114, No. 1, pp. 95-104; XP009173341.

Malmberg, Karl-Johan, et al., "NK cell-mediated targeting of human cancer and possibilities for new means of immunotherapy", *Cancer Immunology Immunotherapy*, 2008; vol. 57, No. 10, pp. 1541-1552; XP019624414A.

Schaeffer, M., et al., "177-P: Maintained tolerance of NK cells expressing inhibitory KIR for non-self ligands in HLA-matched sibling stem cell transplantation", *Human Immunology*, 2009, vol. 70, p. S100; XP026699347.

International Search Report and Written Opinion of the International Searching Authority for PCT/EP2013/068319, dated Oct. 25, 2013, 11 pages.

Vivien Béziat, "Etude de la différenciation terminale des cellules NK basée sur différents modèles cliniques : rôle du CD16, NKG2A, NKG2C et des KIRs" Thesis, Dec. 2010, 3 pages.

Lee et al., "HLA-E Surface Expression Depends on Binding of TAP-Dependent Peptides Derived from Certain HLA Class I Signal Sequences," The Journal of Immunology, 1998, vol. 160, pp. 4951-4960.

\* cited by examiner

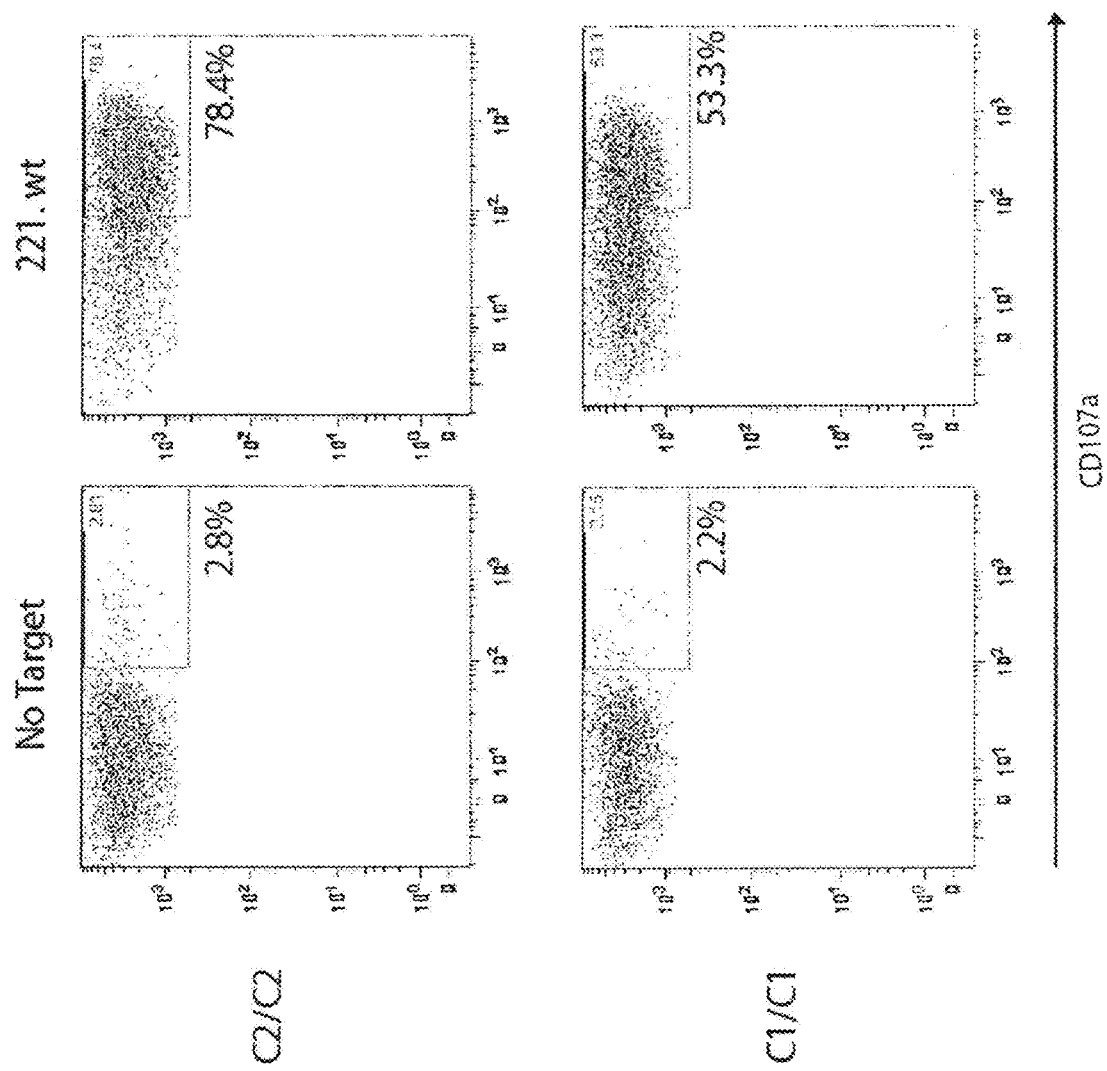

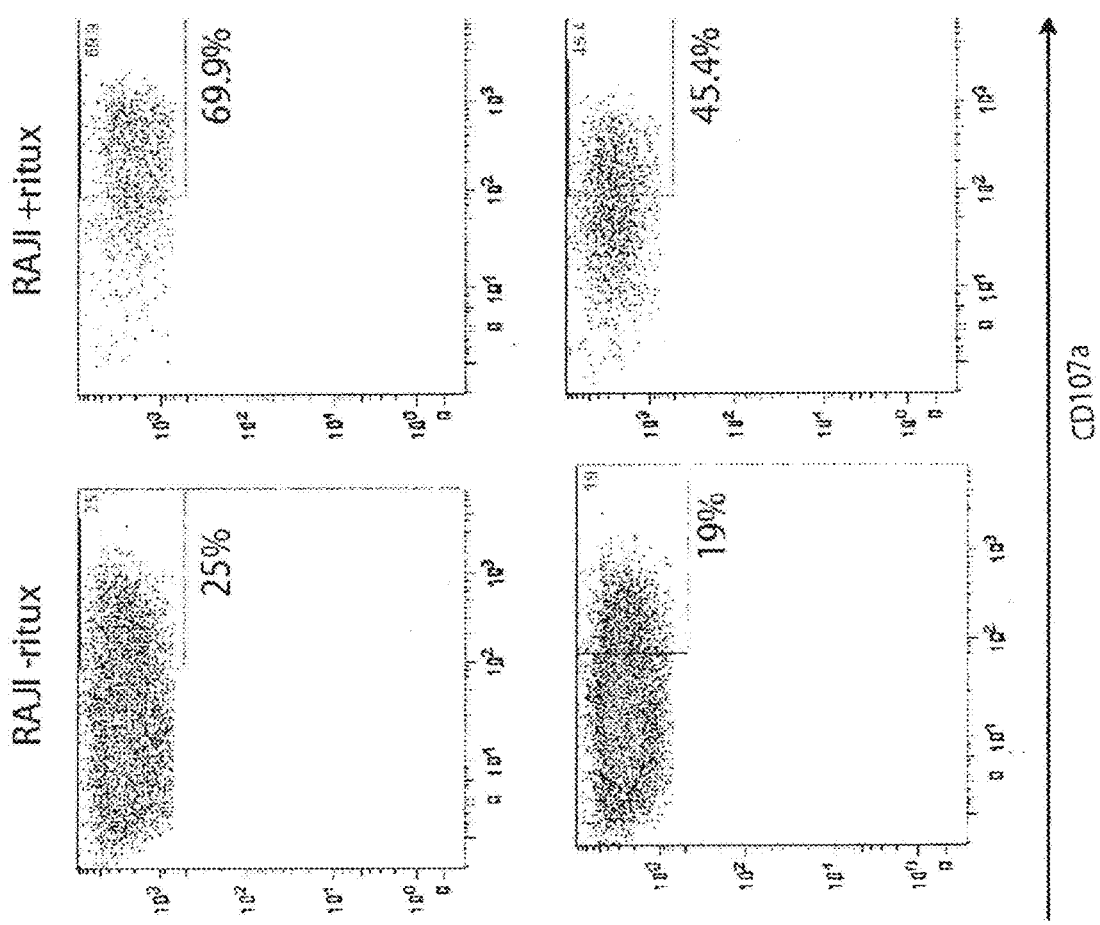

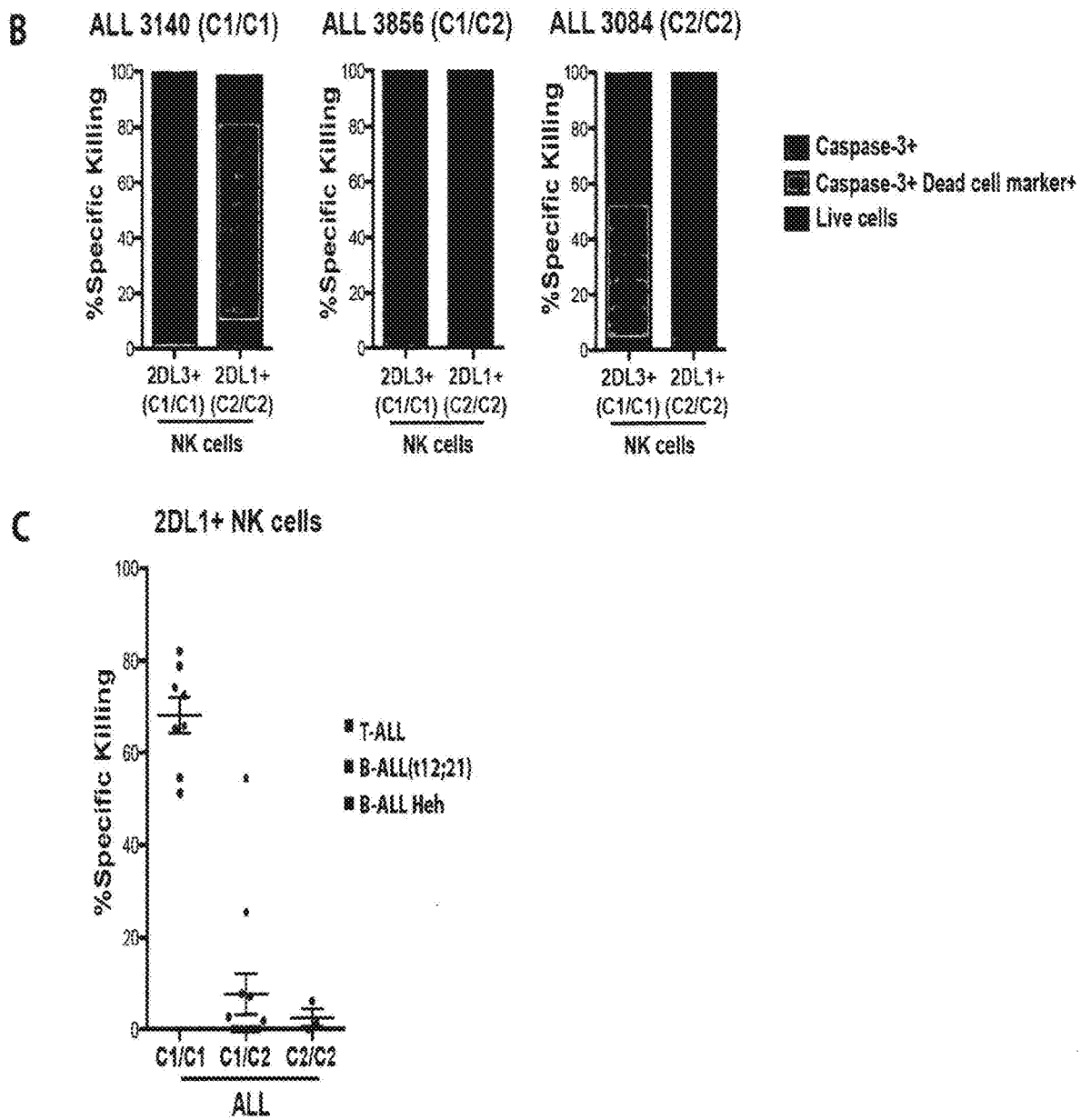

SELECTIVE AND CONTROLLED EXPANSION OF EDUCATED NK CELLS

CROSS REFERENCE TO RELATED APPLICATIONS

This application is a National Phase Patent Application and claims priority to and the benefit of International Patent Application No. PCT/EP2013/068319 filed Sep. 4, 2013, which claims priority to and the benefit of U.S. Provisional Application Ser. No. 61/696,414 filed Sep. 4, 2012, the entire contents of all of which are incorporated herein by reference.

FIELD OF THE INVENTION

The present invention relates generally to immunotherapy. More specifically the present invention relates to NK-cell based therapy against cancer, immunodeficiency, infectious and autoimmune diseases. Methods for expanding a population of cytolytic NK cells are provided, which may be used for therapy. However, such methods may also have non-therapeutic uses, for example in research.

BACKGROUND OF THE INVENTION

Natural Killer Cells

Natural killer (NK) cells represent an important component of innate immunity. NK cells provide rapid responses to virally infected cells and respond to tumour formation.

The function of NK cells is regulated by a vast array of germ-line encoded cell surface receptors that mediate signals for activation or inhibition. Many NK cell receptors are paired with activating and inhibitory counterparts, sharing the same ligand, albeit with different binding affinities. Examples of such paired receptors are the lectin-like heterodimers CD94/NKG2A (inhibitory) and CD94/NKG2C (activating), both of which bind to the non-classical human leukocyte antigen (HLA)-E molecule. Similarly, the killer cell immunoglobulin-like receptor (KIR) gene cluster, located within the leukocyte receptor complex on chromosome 19, encodes fourteen KIR genes with inhibitory (2DL1-3, 2DL5, 3DL1-3), activating (2DS1-5, 3DS1) or dual signaling potential (KIR2DL4). The KIR gene-cluster is divided into group A haplotypes, dominated by inhibitory KIR, and group B haplotypes, containing a varying number of activating and inhibitory KIR. KIR expression is highly variable among individuals and is determined by variation in KIR gene content, copy number, extensive polymorphisms in KIR genes and probabilistic mechanisms involving epigenetic regulation of transcription.

Among the inhibitory KIR, five have well-defined specificities for distinct groups of HLA class I alleles; KIR2DL3 and KIR2DL1 bind to HLA-C1 and HLA-C2, respectively, KIR2DL2 binds to both HLA-C1 and -C2, KIR3DL1 binds to HLA-Bw4, and KIR3DL2 displays peptide-dependent binding to HLA-A3/A11.

NK cells have to undergo an education process, also referred to as licensing or arming, to become functionally competent. Acquisition of full effector function is dependent on the interaction with self MHC class I molecules, which has important consequences for the functionality of the NK cell repertoire in individuals with different HLA backgrounds.

Hence, although inhibitory interactions between KIR and their cognate ligands abrogate the effector phase of an NK cell response, they are also required for the functional education of NK cells. The strength of the inhibitory interactions during NK cell development, and possibly throughout the life-span of the cell, determines the overall functional potential of the NK cell when faced with targets that lack the corresponding HLA class I ligand.

In Gumá et. al *The CD94/NKG2C killer lectin-like receptor constitutes an alternative activation pathway for a subset of CD8⁺ T cells*; Eur. J. Immunol. 2005 35:2071-2080 it is reported that CD94/NKG2C⁺ NK- and T-cell subsets divided in response to stimulation with an HLA class I-deficient tumor cell line transfected with HLA-E.

Further Gumá et. al *Expansion of CD94/NKG2C⁺ NK cells in response to human cytomegalovirus-infected fibroblasts* Blood 2006 107: 3264-3631 discusses the increase of CD94/NKG2C⁺ NK cells in healthy individuals infected with human cytomegalovirus (HCMV).

Della Chiesea et al. *Phenotypic and functional heterogeneity of human NK cells developing after umbilical cord blood transplantation: a role for human cytomegalovirus*; Blood 2012 119(2): 399-410 observed a more rapid NK-cell maturation together with expansion of NKG2C⁺ NK cells in patients experiencing cytomegalovirus reactivation. Lopez-Vergés et al. *Expansion of a unique CD57⁺NKG2C^hi natural killer cell subset during acute human cytomegalovirus infection*; PNAS 2011 108(36): 14725-14732 describe that during human CMV infection there is a preferential expansion of NK cells expressing the activating receptor NKG2C. According to Lopez-Vergés et al. "unlicensed" NK cells proliferated better and more efficiently than educated NK cells. These results supported their earlier findings in mice that uneducated NK cells, lacking self-MHC specific receptors, controlled mouse CMV replication in vivo better than NK cells expressing inhibitory receptors for self-MHC class I. (Orr M T, Murphy W J, Lanier L L. *Unlicensed' natural killer cells dominate the response to cytomegalovirus infection*. Nat Immunol. 2010 April; 11(4):321-7. Epub 2010 Feb. 28).

Different groups of alloreactive NK cells taking into consideration KIR/HLA class I mismatch are discussed in Moretta et. al; *Killer Ig-like receptor-mediated control of natural killer cell alloreactivity in haploidentical hematopoietic stem cell transplantation* Blood 2011 117 (3): 764-771. These alloreactive NK cells are generated in recipients of haploidentical hematopoietic stem cell transplantation (HSCT) and the alloreactive NK subset is detectable 6 to 7 weeks after transplantation and, in most instances, the pattern of expressed KIRs is similar to that originally found in the donor.

Since these NK cells appear after 6 to 7 weeks their antileukemia effect may occur only after this point, which may represent a major limitation, resulting in leukemic relapses.

KIR-HLA mismatch is also discussed in Leung et al. *Determinants of Antileukemia Effects of Allogenic NK Cells*, The Journal of Immunology 2004 172: 644-650 where they explain that the potency of antileukemia effects increases with an increasing number of receptor-ligand mismatch pairs, it is therefore speculated that a donor with a larger number of mismatch pairs may be a better donor. The authors advocate the receptor-ligand model, which encompass the potential alloreactivity of uneducated NK cells in the donor.

It is suggested by Miller et al. in *Successful adoptive transfer and in vivo expansion of human haploidentical NK cells in patients with cancer*; Blood 2005 105: 3051-3057 that haploidentical NK cells can persist and expand in vivo and may have a role in the treatment of selected malignancies used alone or as an adjunct to HCT. Miller et al. demonstrate that adoptively transferred human NK cells derived from haploidentical related donors can be expanded in vivo, further suggesting that prospective selection of KIR ligand-mismatched donors is warranted when possible.

In Björklund et al. *NK cells expressing inhibitory KIR for non-self-ligands remain tolerant in HLA-matched sibling stem cell transplantation*; Blood 2010 115: 2686-2694 the authors discuss the major contribution of NKG2A+ NK cells to the functional response early after transplantation. NKG2A receptors are expressed early during NK-cell differentiation and are expressed on most CD56$^{bright}$ NK-cells. According to this article NKG2A+ NK cells predominate the functional responses in donors with low overall frequencies of KIR expression.

There is a need for more specific and potent tumour cell killing in cancer treatment today. There is also a need for cancer treatment for those patients who are refractory to conventional chemotherapy, or to those with an indication for allogeneic stem cell transplantation but who lack a stem cell donor, or are threatening relapse following cord blood transplantation when no donor lymphocytes are available for donor lymphocyte infusion.

SUMMARY OF THE INVENTION

A primary objective of the present invention is to selectively expand, in a controlled way, highly cytolytic NK cells of a given KIR specificity. These cells may be transferred to patients and enable potent tumor cell killing.

The present invention presents a strategy based on stimulation tof paired inhibitory and activating receptors on NK cells, taking advantage of the previously unknown role for education in the survival and proliferation of cells stimulated in this way. The invented strategy is unique, since it yields cells with four beneficial properties for targeting of cancer cells 1) It enriches for cells with the activating NKG2C receptor to a ligand broadly expressed on tumors (HLA-E). 2) It enriches for cells that are negative for the inhibitory NKG2A receptor. 3) The strategy expands cells with a predictable expression pattern of inhibitory KIRs and is therefore personalized to fit the HLA class I of the patient, promoting NK cell-mediated alloreactivity or targeting of HLA class I negative target cells. 4) The expanded cells undergo a differentiation process and become highly cytolytic and very potent in mediating antibody-dependent cellular cytotoxicity (ADCC).

More specifically, the method presented herein may be used in the therapy of various immunodeficiency diseases and cancers including but not limited to refractory lymphoid malignancies including malignant lymphoma, adult and childhood acute lymphoid leukemia, acute myeloid leukaemia, myelodysplastic syndrome, hemophagocytic lymphohistiocytosis (HLH), familial hemophagocytic lymphohistiocytosis (FHL), infections and autoimmune diseases.

The method presented herein is also useful for patients that are refractory to conventional chemotherapy or in those with indication for allogeneic stem cell transplantation but lacking a stem cell donor or are threatening relapse following cord blood transplantation when no donor lymphocytes are available for donor lymphocyte infusion.

Donors are selected based on their KIR ligand status and leukocytes are separated therefrom, for example apheresis of a donor is performed to obtain a large number of leukocytes. NK cell isolation may then optionally be performed, or a leukocyte-containing preparation, e.g. PBMC or another cell fraction containing leukocytes may be used.

NK cells are then expanded in the presence of the HLA-E molecule or another stimulator of NKG2C, e.g., a monoclonal antibody (mAb), against NKG2C. As described in more detail below, although it is preferred to use HLA-E, the natural ligand for the NKG2C receptor, other stimulators may be used, that is any stimulator of the NKG2C or NKG2A receptor. As also described in more detail below, the HLA-E ligand is used or provided (presented to the cells) in a form in which it is recognised and may be bind to the cell surface NKG2C and NKG2A receptors. The proliferation following stimulation via NKG2C leads to the preferential accumulation of NK cells expressing self-specific KIRs. There is no other way to enrich a given KIR population as efficiently.

These enriched cells can then be transferred to a patient. Transfer of NK cells over HLA barriers triggers alloreactivity and enables tumour killing. Transfer of the cells to HLA-matched patients where the target cells lack the relevant HLA class I molecule yield a high degree of specificity, since all other "normal" cells are spared.

An object of the present invention is to provide a method for selectively obtaining cytolytic differentiated NKG2A⁻ NKG2C⁺ (commonly referred to as memory-like) NK cells with a given KIR specificity.

Another object of the present invention is to provide a composition comprising such cytolytic differentiated NKG2A⁻ NKG2C⁺ NK cells with a given KIR specificity.

Another object of the present invention is to use the cytolytic differentiated NKG2A⁻NKG2C⁺ NK cells with a given KIR specificity for therapy.

Another object is to genetically modify the cytolytic differentiated NKG2A⁻NKG2C⁺ NK cells with a given KIR specificity to express chimeric receptors, chemokine receptors, for optimized targeting of desired cell types in distinct clinical settings including cancer, infectious diseases, immunodeficiencies and autoimmunity.

Another object is to combine cytolytic differentiated NKG2A⁻NKG2C⁺ NK cells with a given KIR specificity and tumour specific antibodies to achieve better ADCC in the abovementioned clinical settings.

Another object is to combine cytolytic differentiated NKG2A⁻NKG2C⁺ NK cells with strategies of genetically engineering, including transfer of chimeric antigen receptors, T cell receptors by means of mRNA electroporation, lentiviral vectors, retroviral vectors, transposon technologies.

Other objects and advantages of the present invention will become obvious to the reader and it is intended that these objects and advantages are within the scope of the present invention.

To address these various objects, the present invention in a first aspect provides an in vitro method for expanding natural NK cells of a given KIR specificity for transfer into a patient for use in therapy of said patient, said method comprising:

(a) selecting a donor having NK cells of a said given KIR specificity, selected with respect to the HLA class I type of the patient, and optionally with respect to the condition to be treated;

(b) providing leukocyte cells from said donor, wherein said leukocytes comprise NK cells;

(c) contacting said donor NK cells with a stimulator of one or both of the paired receptors CD94/NKG2C and CD94/NKG2A, thereby selectively to expand NK cells having said KIR specificity which are NKG2C positive and NKG2A negative, to produce a population of cells comprising said expanded NK cells.

Other aspects of the invention include a cell population obtainable by such a method, a pharmaceutical composition comprising such a cell population and the use of such a cell population in therapy, more particularly for transfer to a patient to treat a condition responsive to therapy with cytolytic NK cells.

The novel expansion method of the present invention may also have uses outside the therapeutic/medical arena (i.e non-medical uses), and may for example be used to generate NK cells for research, or to investigate immune reactions involving NK cells etc. In this case there may not be a need to generate NK cells with reference to a particular patient as such (i.e. "fitted to a patient or intended cell recipient), but nonetheless a given or desired KIR specificity may be selected.

Accordingly, at its broadest, the invention can be seen to provide an in vitro method for expanding natural killer (NK) cells of a given KIR specificity, said method comprising:
(a) selecting a donor having NK cells of a said given KIR specificity;
(b) providing leukocyte cells from said donor, wherein said leukocytes comprise NK cells;
(c) contacting said donor NK cells with a stimulator of one or both of the paired receptors CD94/NKG2C and CD94/NKG2A, thereby selectively to expand NK cells having said KIR specificity which are NKG2C positive and NKG2A negative, to produce a population of cells comprising said expanded NK cells. As noted above, the method of the invention involves generating cytolytic NK cells of a given KIR specificity, which specificity is determined by the donor. Thus the KIR specificity is a selected, or desired, or defined, or pre-determined specificity, and the donor is chosen with this in mind, having regard to the HLA class I type of the patient (the intended recipient of the expanded NK cells). Thus, to ensure that the obtained NK cells are reactive to (cytolytically active against) the target cells in the patient, in many cases the donor is selected to have an HLA-class I mismatch at one or more groups of HLA class I allele(s), more particularly at one or more HLA class I alleles relevant for the KIR of the donor cells. In other words, the donor is mismatched at one or more alleles corresponding to the HLA-class I alleles which bind to the inhibitory KIR expressed on the donor NK cells. However, as noted above in some situations a match may be acceptable (i.e. the donor may be matched to the patient at HLA class I), where the target cells do not express or only express low or minimal (negligible or insignificant) amounts of HLA class I molecules.

"Target cells" will be understood as the cells in the patient to which it is desired to target the NK cells, e.g. cells to be removed or abrogated, for example cancer or tumour cells, or infected cells, or undesirable immune cells. The target cell will of course depend on the condition to be treated.

As described and explained further below, the NK cells which are selectively expanded are educated NK cells, that is NK cells which express self-specific KIR, namely KIR specific for self HLA class I molecules ("self" with respect to the donor). It will be understood therefore that the donor leukocytes comprise at least some NK cells which are educated, and it is these educated NK cells which are selectively expanded to produce a population of cells comprising cytolytic educated NK cells of a given (i.e. desired) KIR specificity which are NKG2C$^+$NKG2A$^-$. Such cells will be highly specific against HLA-mismatched target cells, or target cells lacking HLA class I. Donors may be selected which have an increased proportion of educated NK cells, or increased NK cells of a desired KIR specificity, based e.g. on their past clinical history, for example as detailed below, donors exposed to CMV demonstrate increased levels of NK cells expressing self HLA class I molecules.

The selective expansion of the NKG2C$^+$NKG2A$^-$ NK cells of the desired given KIR specificity means that the resulting cell population obtained by the method comprises an increased amount or proportion of the desired cytolytic NK cell type. In other words the proportion or amount of the desired NKG2C$^+$NKG2A$^-$ NK cells of the given KIR specificity is selectively increased. The resulting cell population is thus enriched in such cells. It will be understood therefore that "selectively expanding" means enriching the cell population in the desired cells, as specified above. The cell population may thus predominantly comprise NKG2C$^+$NKG2A$^-$ NK cells of the selected given KIR specificity. Such an enriched cell population may for example comprise at least 50, 60, 70, 80 or 90% of the NKG2G$^+$NKG2A$^-$ NK ells as a percentage of total cells in the cell population (i.e. of total cells in the resulting cell product).

BRIEF DESCRIPTION OF THE DRAWINGS

FIG. 4. Specificity of the expanded cells. NK cells expanded by the method disclosed herein from an HLA-C1 homozygous donor were exposed to 721.221 cells transfected with HLA-C1 (C1+) or HLA-C2 (C2+). Degranulation was monitored as surface expression of CD107a.

FIG. 6 High cytolytic potential of NK cells expanded according to the present invention. NK cells from HLA-C1 or HLA-C2 homozygous donors were expanded as described in this invention and then stimulated by HLA class I negative 721.221 wild type cells (221.wt), the B cell lymphoma cell line Raji in the presence or absence of the ant-CD20mAb Rituximab (ritux). Degranulation was monitored as surface expression of CD107a.

NK cells expanded according to the present invention from a HLA-C1/C1 donor were stimulated with leukemic blast cells from two patients with distinct HLA types. NK cell degranulation was monitored by surface expression of CD107a.

Figure 8:
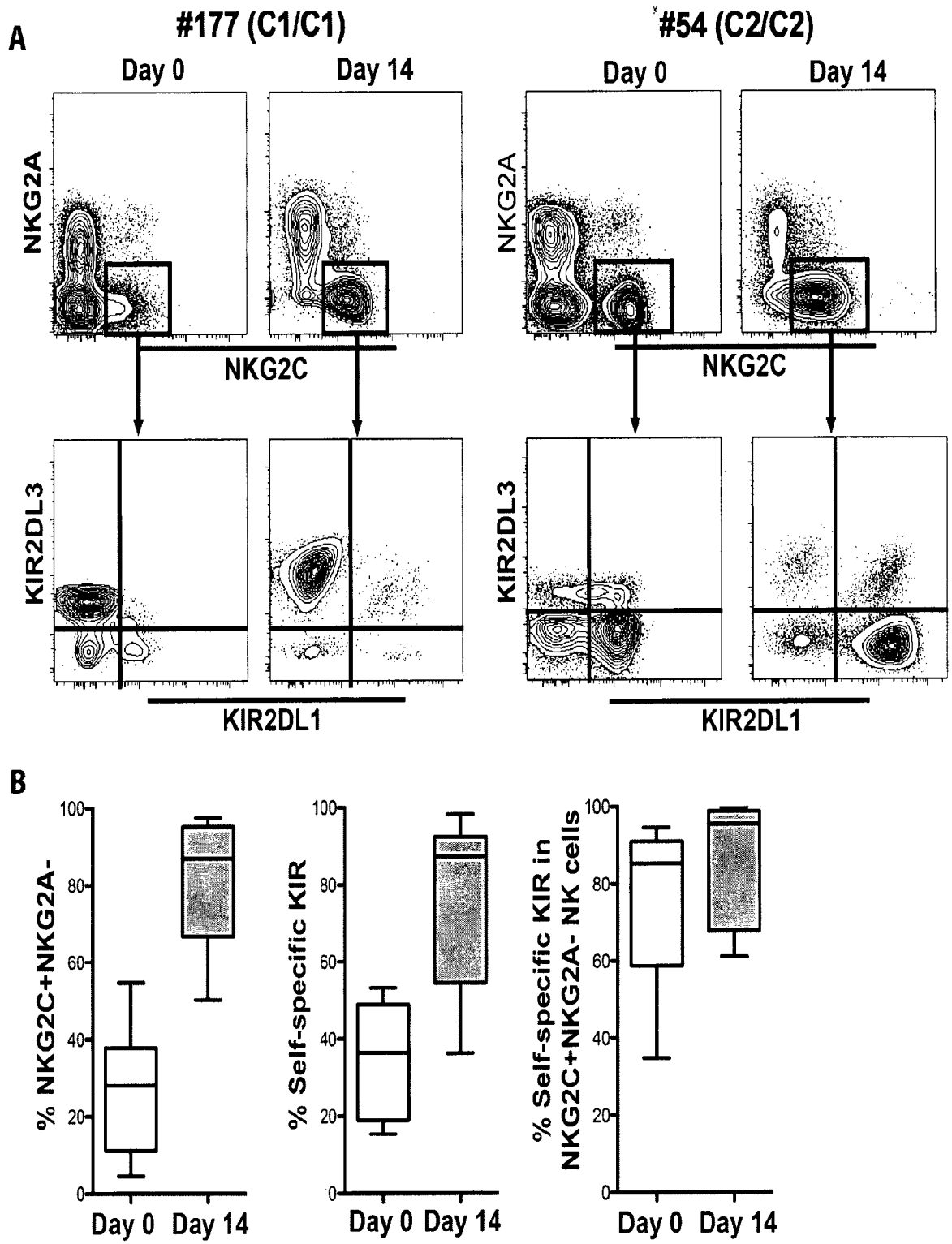

FIG. 8. Selective and controlled expansion of educated NK cells. NK cells were isolated and cocultured with irradiated 721.221 cells transfected with HLA-E and the HLA-A leader sequence (221.AEH) in IL-15 for 14 days. Representative FACS plots showing the KIR repertor in NK cells from (A) a C1/C1 donor and (B) a C2/C2 donor at day 0 and day 14. (B) Summary of the expansion (left panel) and skewing (middle and right panel) in NK cell/221.AEH co-culture experiments from HCMV seropositive donors (n=14).

Figure 9:
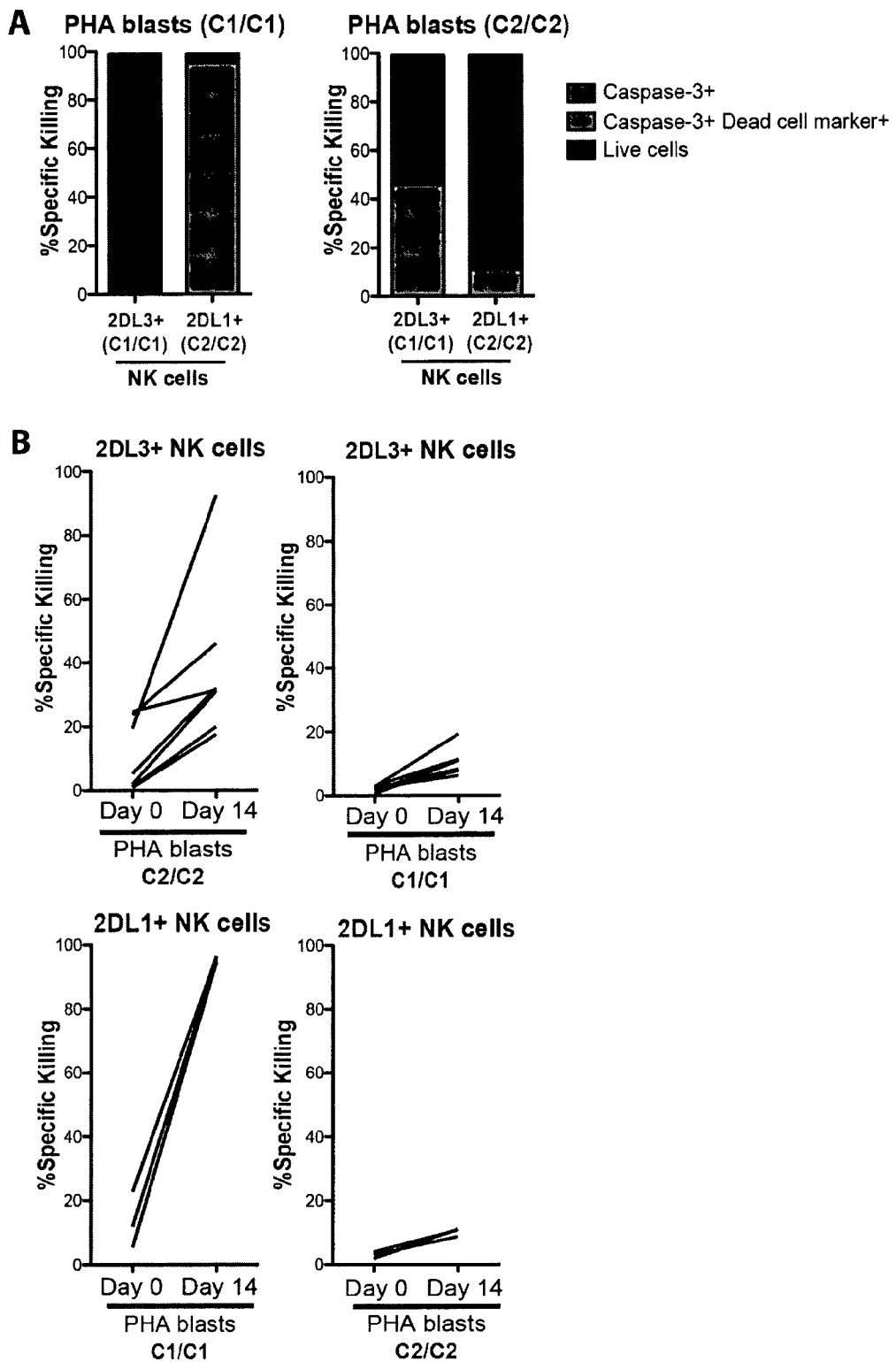

FIG. 9. Specificity and efficacy of expanded NK cells. NK cell-mediated killing was assessed in a flow cytometry-based assay by monitoring caspase-3 activity and staining of a live/dead cell marker (DCM) in PHA blasts following co-incubation with NK cells at E:T ratio 5:1 for 4 hours. (A) Representative graphs showing killing of PHA blasts in HLA-C matched and mismatched settings. (B) Killing of mismatched PHA blasts by expanded NK cells Day 14) compared to NK cells stimulated with IL-15 over night (Day 0).

Figure 10:
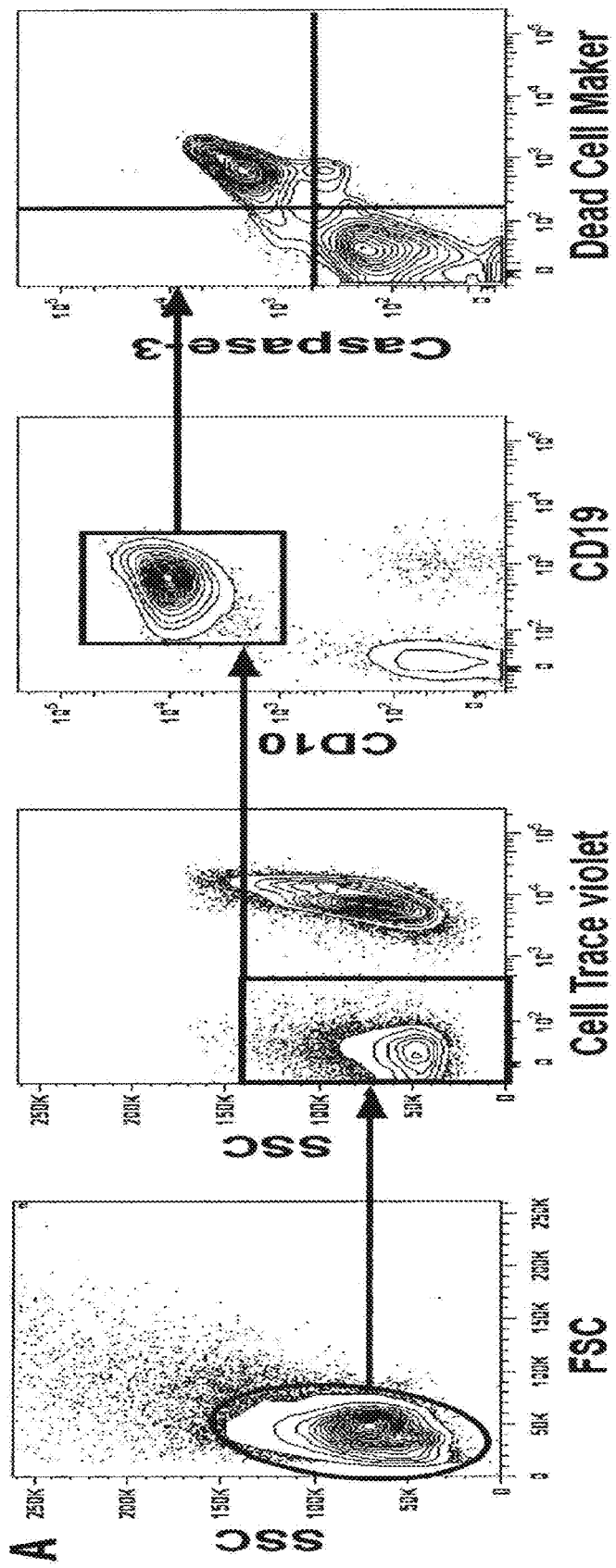

FIG. 10. Selectively expanded NK cells efficiently lyse primary blasts from children with acute lymphoblastoid leukemia. Expanded NK cells were tested against primary ALL blasts from 24 children in a FACS-based killing assay at an E:T ratio of 5:1 for 4 hours. (A) Representative FACS plots showing the gating strategy to detect primary ALL blasts after coculture with NK cells. NK cells were stained with CellTrace violet and excluded from the analysis. Markers to identify the ALL blasts were determined according to the minimal residual disease phenotype (NOPHO panel) at the time of diagnosis. (B) Representative graphs illustrating the killing of subtypes of ALL blasts. (C) Summary showing killing of primary ALL blasts with the indicated HLA-C genotype by expanded NK cells expressing KIR2DL1.

Figure 11:
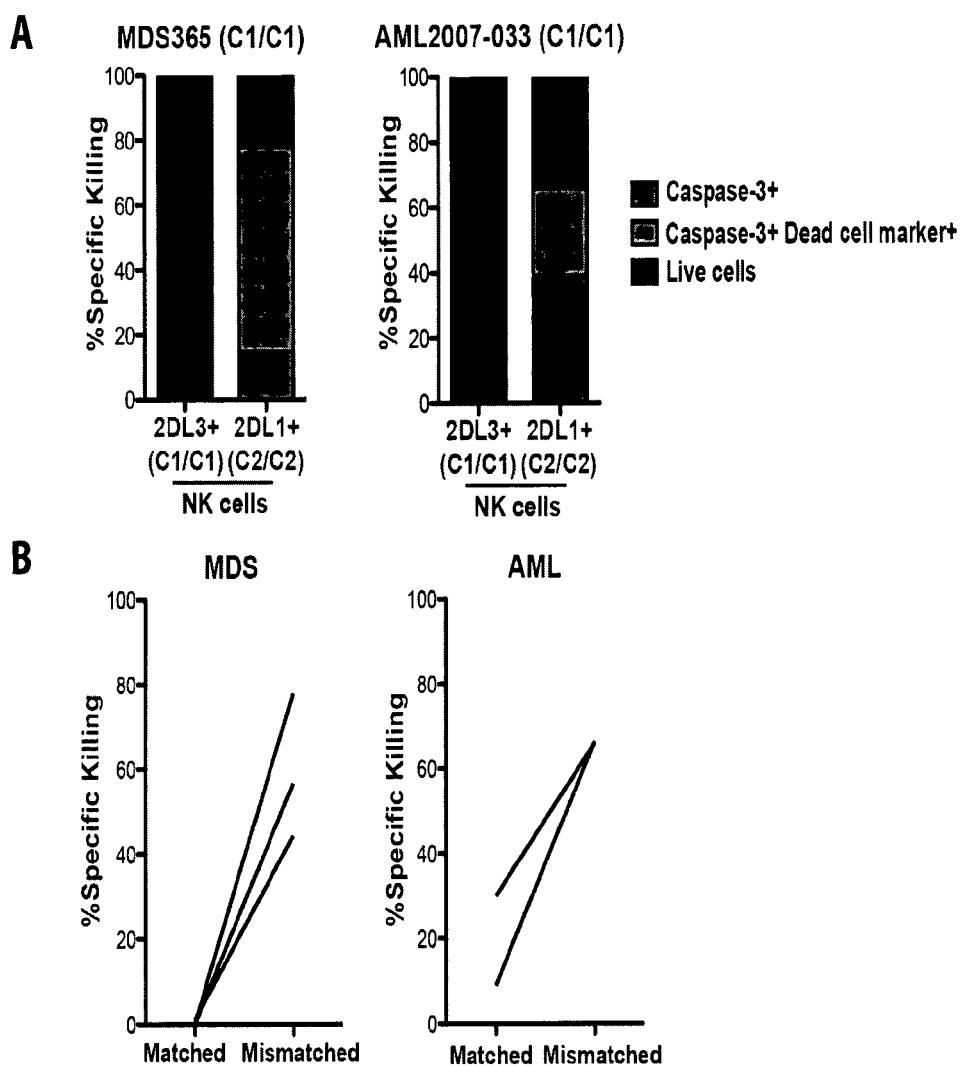

FIG. 11. Targeting of high-risk myeloid malignancies. A) shows an example of specific killing of CD34+ blasts from patients with myelodysplastic syndrome (MDS) (left) and acute myeloid leukemia (AML). (B) Specific killing of matched and mismatched AML (n=2, one patient was C1/C1 and one C2/C2) and MDS blasts (n=3, all C1/C1).

Figure 12:
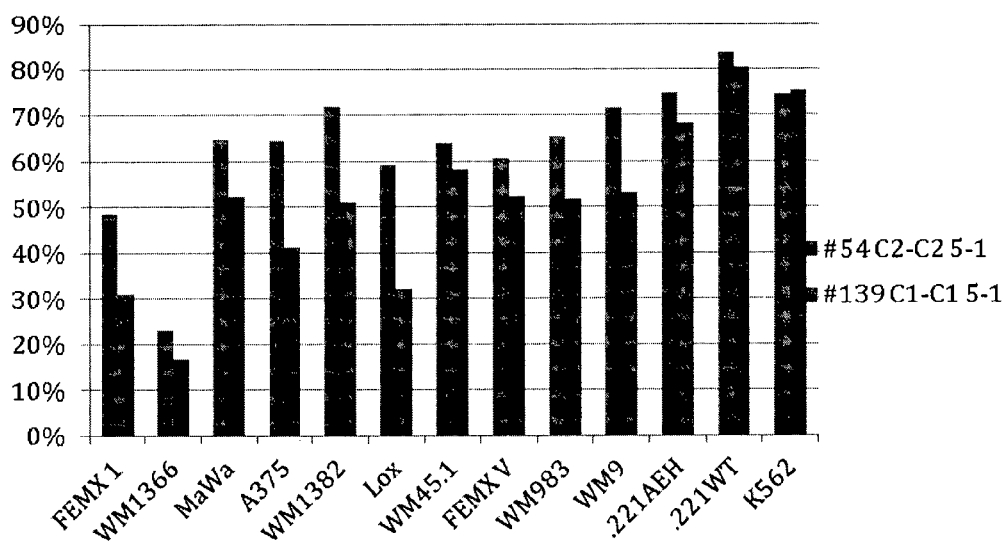

FIG. 12. Targeting of malignant melanoma. Shows the results of a standard Cr51-release assay against a range of melanoma cell lines obtained from ATCC.

Figure 13:
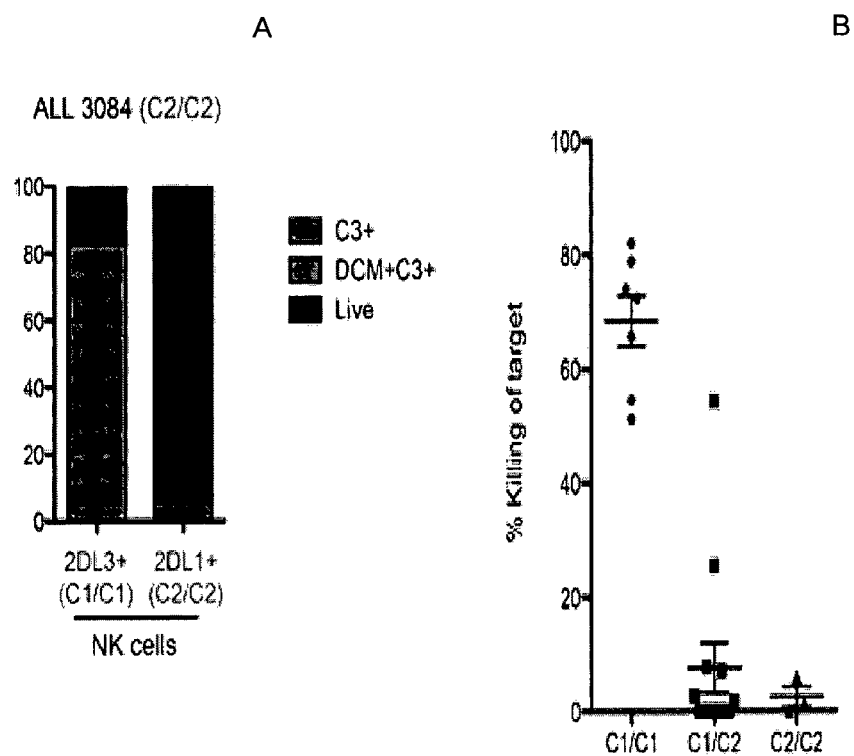

FIG. 13. Selective targeting of HLA-C2/C2 targets by KIR2DL3+KIR2DS1+ NK cells. A) shows an example of killing and specificity of primary ALL blast cells by NK cells expressing KIR2DL3 and KIR2DS1. B) shows expanded NK cells that were tested against a panel of primary ALL targets with the indicated HLA-C genotype.

DETAILED DESCRIPTION OF THE INVENTION AND PREFERRED EMBODIMENTS THEREOF

KIR/HLA mismatched donors for cancer treatment has been discussed previously in the setting of allogeneic HSCT or adoptive NK cell therapy, where the patient in most instances, following in vivo expansion of NK cells obtain KIR expression patterns similar to those in the donor and this is not until approximately 6 weeks after transplantation/cell therapy. During such in vivo expansion it is not possible to selectively expand the NK cells in a controlled way as the inventors of the present invention propose to do before NK cells are administered to the patient. An in vivo expansion is not a controlled expansion where it is possible to selectively choose the most appropriate NK cells for best treatment.

In vitro expanded NK cells have been used for treatment of hyperproliferative disorders, however these cells were not expanded in the presence of feeder cells expressing HLA-E and consequently such expanded cells will be NKG2A$^+$. Due to the presence of the inhibitory NKG2A receptor such cells will not be as efficient and potent tumor killing cells as the NK cells presented herein.

WO 99/28748 describes the use of HLA-E for detecting, separating and targeting toxins to CD94/NKG2$^+$ cells. NK cells are believed to have an anti-tumour cell activity and according to the inventors a marker for progress of therapy, or simple prognosis, can be provided by monitoring NK cell numbers and optionally their state of activation. The invention described in WO 99/28748 provides methods of selecting HLA-E binding NK cells from a mixed cell population. The selected cells can be expanded in vitro and returned to the patient. Such treatment may be effective in some serious infections or cancer where a growth deficiency of these cells is associated with poor prognosis.

Igarashi et al. *Enhanced cytotoxicity allogeneic NK cells with killer immunoglobulin-like receptor ligand incompatibility against melanoma and renal cell carcinoma cells*; Blood 2004 104: 170-177 and WO 2006/050270 describe the effects of KIR ligand mismatched NK cell populations against solid tumors. These publications also describe enriched NK cell populations cloned from the blood of cancer patients or healthy donors homozygous for HLA-C alleles in group 1 or group 2. The strategy proposed in Igarashi et al., involves expansion of NK cells on feeder cells expressing given HLA class I molecules.

Siegler et al. *Good manufacturing practice-compliant cell sorting and large-scale expansion of single KIR-positive alloreactive human natural killer cells for multiple infusions to leukemia patients* Cytotherapy 2010 12: 750-763 expand alloreactive NK cells of single KIR.

However, the strategy taught by Igarashi et al and Siegler et al. differ from the current invention since their strategy will generate cells that express NKG2A and does not consider the education status of the donor.

HLA-E is a ligand for the activating NK cell receptor NKG2C as well as for the inhibitory NK cell receptor NKG2A. It has previously been suggested that HLA-E interaction with NKG2C might contribute to drive the proliferation of NKG2C$^+$ cells in CMV infected patients. However HLA-E has not previously been used for controlled selective in vitro expansion of NK cells with a given KIR specificity.

HLA-E binding has previously been used to detect NKG2$^+$ cells, however this has not been selective for different types of NKG2 cells. In WO 99/28748 HLA-E is used in cancer diagnostics by counting numbers of NK cells but gives the reader no clue about how to use HLA-E for selective expansion of NK cells. In WO 99/28748 they have a mixed population of NKG2C and NKG2A, which is not applicable in this invention where it is important to obtain NKG2A$^-$NKG2C$^+$ NK cells. NKG2C acts as an activating receptor and it is therefore desirable with NKG2C positive NK cells in the present method, since this will promote tumor cell killing. NKG2A however is an inhibitory receptor and the inventors of the present invention disclose a strategy for how to select NKG2A negative cells. If both NKG2A and NKG2C are present on the NK cells, NKG2A and the inhibitory effect will be dominating. Therefore it is important to only select NK cells that are NKG2C positive and NKG2A negative. This is only a small subpopulation of the NK cells and the inventors disclose a novel and inventive strategy to select these specific cells and enrich them to high numbers.

No one has hitherto thought of selecting this certain subset of NK cells for this type of therapy, previously donors with a large population of mismatched KIR NK-cells have been sought. The invented method opens up a way of generating such cells from any donor and will generate more controlled expansion of potent NK cells for therapy.

The inventors of the present invention have revealed that NK cell education promote the survival and expansion of NKG2C$^+$ NK cells in vitro, this is contrary to previous findings presented by Lopéz-Vargas et al. who allege such an expansion would be driven by less constrained uneducated NK cells (lacking inhibitory receptors to self).

The present invention presents a new way of selectively expanding highly cytolytic NK cells of a given KIR specificity. This expansion is personalized to fit the HLA class I type of the patient, thereby promoting NK cell-mediated alloreactivity. Cytolytic NK cells are expanded which are reactive with target cells in the patient to be treated. The method for expanding NK cells presented herein is novel and builds on the discovery that education by self-specific inhibitory KIRs promotes the survival and expansion of NK cells stimulated via NKG2C. The invention is partly counterintuitive since 1) there are conflicting data on the expression of KIRs on NKG2C$^+$ NK cells and 2) since it involves stimulation of bulk NK cells containing a mixture of NKG2A$^+$ and NKG2C$^+$ NK cells where the inhibitory interaction is known to dominate when stimulation occurs on the same cell. In scenarios where HLA-E expression is absent or low, in vitro expansion protocols yield high frequencies of NKG2A$^+$ NK cells. Hence, the presence of HLA-E in the culture serves two purposes at the same time: 1) stimulates the expansion of NKG2C$^+$ NK cells expressing self-specific KIRs and 2) inhibit the expansion of NKG2A$^+$ NK cells with a broader KIR repertoire.

This completely new way of expanding NK cells with given specificity enables more specific and potent tumor cell killing. The NK cells of the present invention can effectively be used in therapy, including but not limited to therapy against cancer, including but not limited to refractory lymphoid malignancies such as malignant lymphoma, adult and childhood acute lymphoid leukemia, since they are selected to have a certain KIR specificity and at the same time are selected to be NKG2A negative and will therefore be very potent tumor killers. Further the use of these expanded NK cells in treatment could fill a gap for patients that are refractory to conventional chemotherapy or in those with indication for allogeneic stem cell transplantation but lacking a stem cell donor or are threatening relapse following cord blood transplantation when no donor lymphocytes are available for donor lymphocyte infusion. Another important application of the cells is in the KIR ligand-matched (including autologous and fully HLA-matched) setting when the scope is to target cells that have low or absent levels of the relevant HLA class I molecule (recognized by the selective KIR$^+$ expansion). Examples of such settings include but are not limited to metastatic melanoma and neuroblastoma.

CMV Skews Human KIR Repertoires

Figure 1:
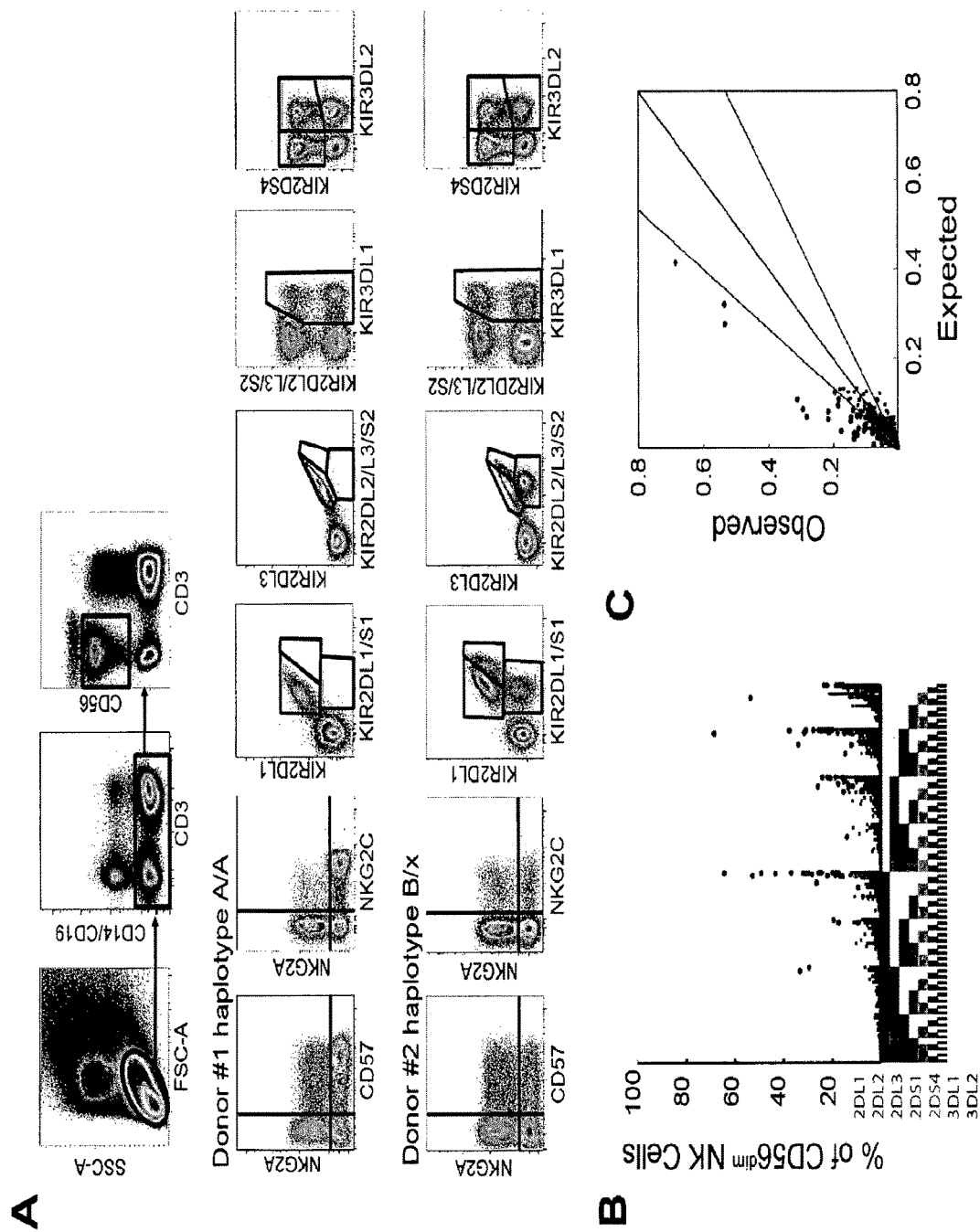
FIG. 1. Characterization of human NK cell MR repertoires. (A) 14-color flow cytometry panel for assessment of KIR2DL1, KIR2DL2/S2, KIR2DL3, KIR3DL1/S1, KIR2DS4, KIR3DL2 expression in CD56$^{dim}$ NK cell subsets expressing NKG2A, NKG2C, and/or CD57. Representative examples of stainings in KIR haplotype A homozygous and haplotype B/X donors are shown. (B) Frequency of CD56$^{dim}$ NK cells expressing the 7 analyzed KIRs and the 128 possible combinations thereof in 199 healthy donors. The presence of one KIR in a combination is represented by a color code below the graph: 2DL1 (dark blue), 2DL2/S2 (purple), 2DL3 (red), 2DS1 (light blue), 2DS4 (orange), 3DL1 (green), 3DL2 (black). Red dots represent statistical outliers as defined by Chauvenet's criterion.

The inventors of the present invention have determined expression patterns on NK cells in a cohort of 204 healthy donors by 14-color flow cytometry (FIG. 1A). An unbiased exploratory analysis of expression-frequencies was made of the relative sizes of all 128 possible combinations of the seven KIR analyzed (FIG. 1B). Among the 25,472 KIR expression frequencies in the 204 donors, the inventors identified 71 statistical outliers (in 60 donors) from a Gaussian distribution, as determined by Chauvenet's criterion (FIG. 1B, red dots). Expression of KIR at the cell surface of NK cells is stochastic and the coexpression of, for example, two KIR can be calculated from their individual frequencies in accordance with the product rule, assuming random association of two independent events. However, KIR expression of the outliers deviated significantly from the product rule, suggesting that such subsets represented cells that had undergone a "clonal-like" expansion in vivo (FIG. 1C).

Figure 2:
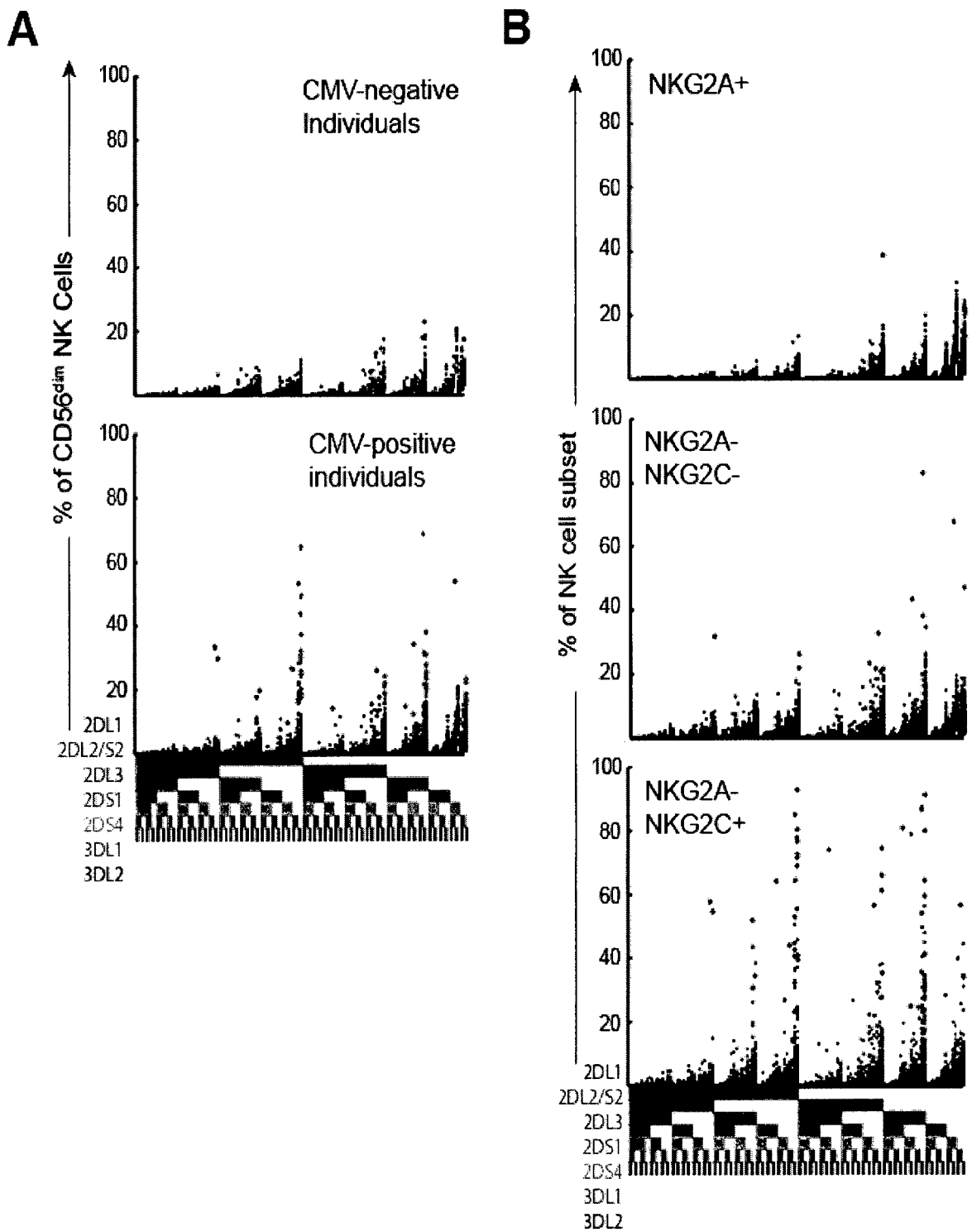
FIG. 2. Dissecting the origin of the expanded MR subsets. (A) Stratification of the cohort into CMV-seronegative (top, n=48) and CMV-seropositive individuals (bottom, n=151). Red dots represent statistical outliers as defined in FIG. 1B. (B) Frequency of donors with one or more outliers. Stratification based on CMV-serology.

Because CMV is known to cause dynamic changes in the NK cell compartment in both mice and humans, the inventors stratified the present cohort on the basis of seropositivity for CMV (FIG. 2A). Strikingly, outliers representing expansions of specific subsets were almost exclusively found in CMV-seropositive individuals (FIGS. 2A and B). Only two out of 48 CMV-seronegative donors displayed outliers.

These results reveal the potential of high-resolution KIR phenotyping for tracing adaptation of NK cells to viral infection. Intriguingly, in healthy individuals, the occurrence of NK cell expansion correlated strongly with past CMV infection.

CMV Induces Expansion of NK Cells Expressing Self-Specific KIR

Figure 3:
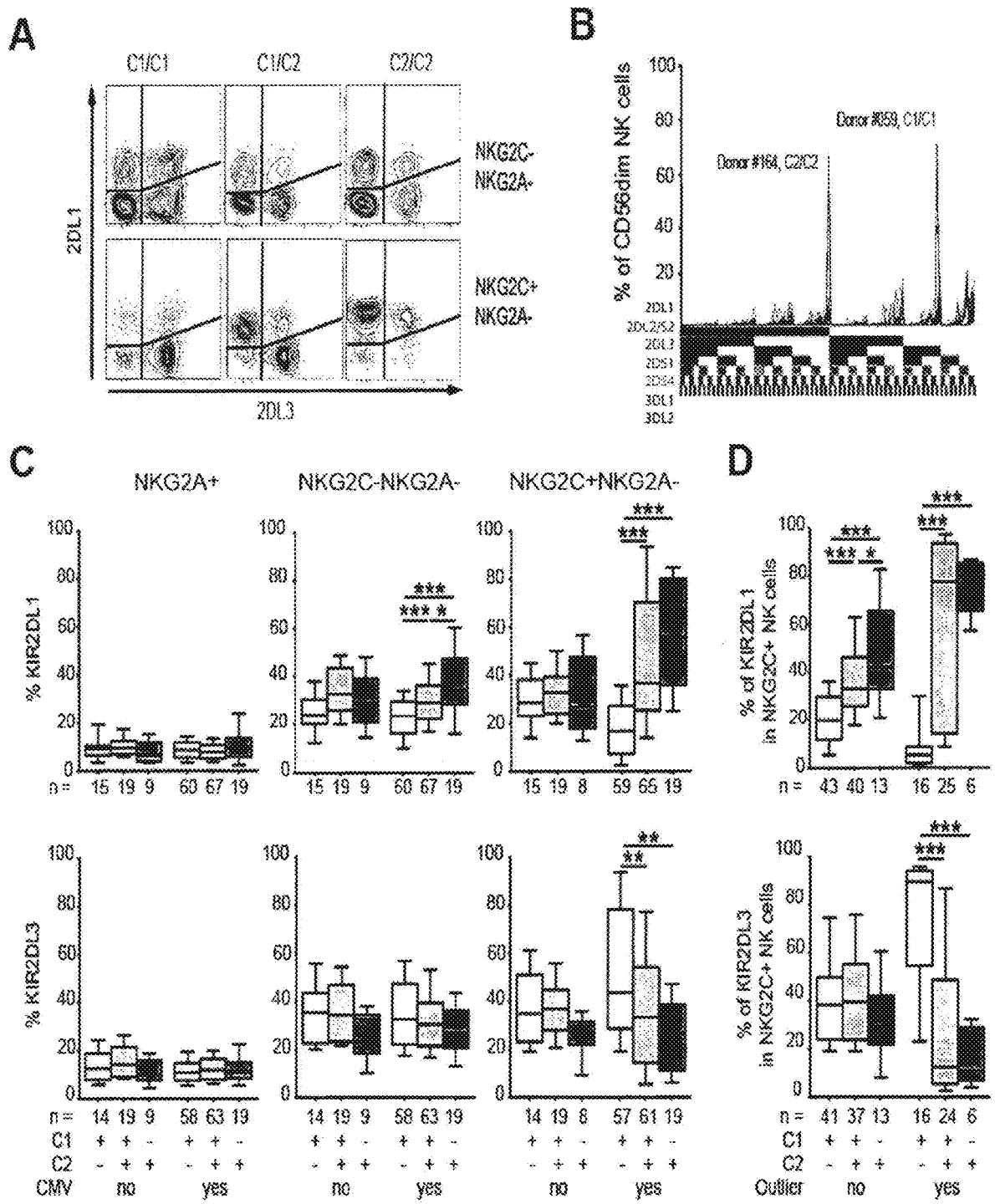
FIG. 3. Influence of cognate- (self-) HLA class I molecules on the MR expression on the expanded cells. (A) representative plot of KIR2DL1 and KIR2DL3 expression in NKG2C$^-$NKG2A$^-$ (top row) and NKG2C$^+$NKG2A$^-$ (bottom row) CD56$^{dim}$ NK cell subsets. Three donors (HCMV seropositive donors) with different HLA genotype are depicted: C1/C1 (left), C1/C2 (middle) and C2/C2 (right). The color-coding illustrates KIR and their cognate HLA-ligands. (B) Shown are two extreme examples of KIR repertoires in donors homozygous for C1/C1 and C2/C2 with skewing towards expression of KIR2DL3 and KIR2DL1, respectively overlaid on the 48 random repertoires in HCMV-seronegative individuals (n=48). (C) The aggregated effect of HLA class I (C1/C1 white bars, C1/C2 light grey bars, and C2/C2 dark grey bars) on KIR expression in all donors was examined by plotting frequencies of KIR2DL1 (top) and KIR2DL3 (bottom) in distinct NK cells subsets: NKG2A$^+$ (left), NKG2C$^-$NKG2A$^-$ (center) and NKG2C$^+$NKG2A$^-$ (right). Donors were stratified based on HCMV serology and HLA-background. (D) The effect of HLA class I on KIR expression in individuals with and without evidence of NK cell expansion. (E) NK cells labeled with CFSE and cultured for 7 to 14 days with 20 ng/ml of IL-15 alone or together with irradiated 721.221 wt or 721.221 HLA-E cells. At day 7 or 14 cells were assessed for KIR and NKG2/C expression.
Figure 3:
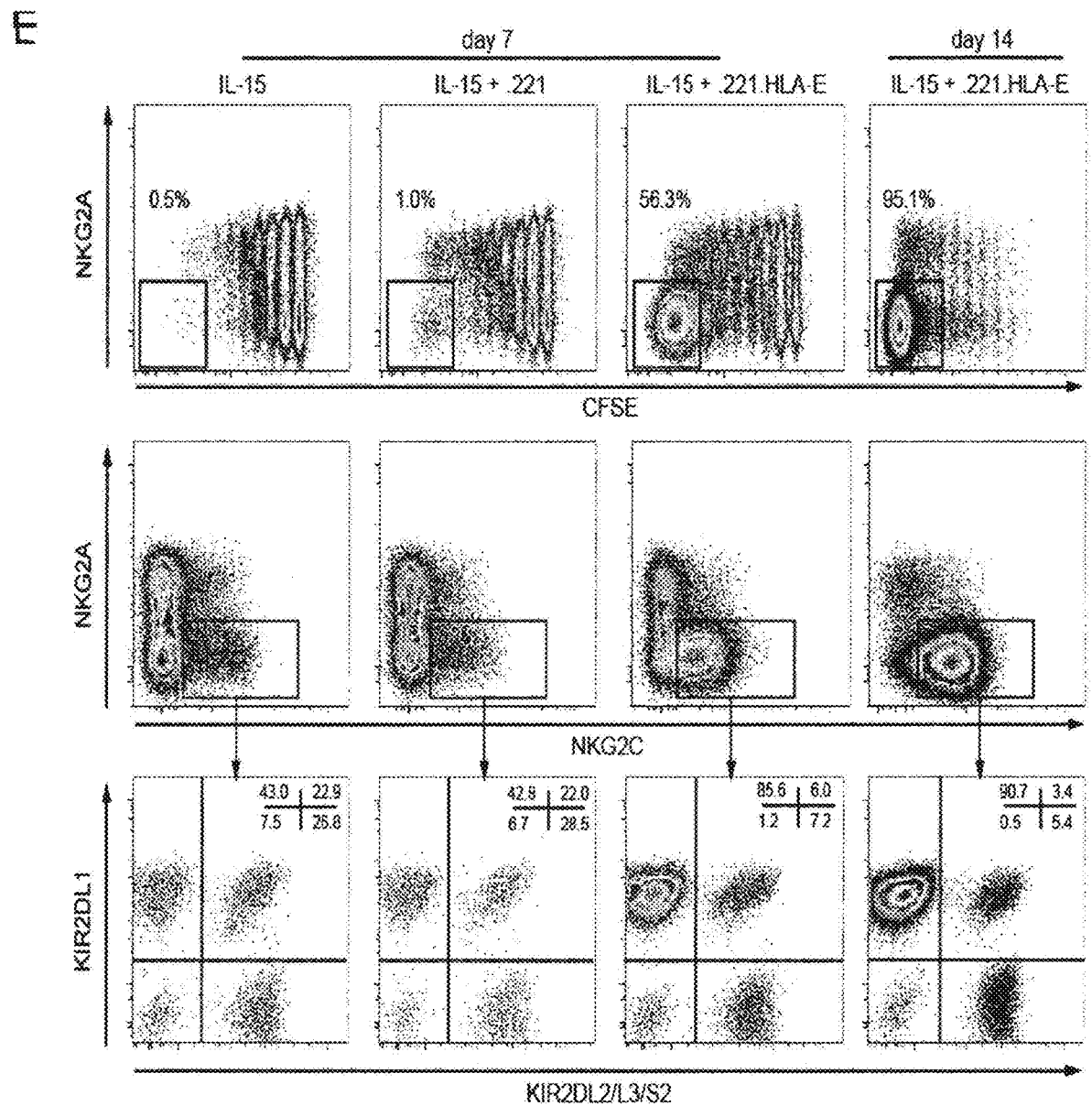

Because most of the expanded subsets expressed at least one HLA-C-binding inhibitory KIR, namely KIR2DL1, KIR2DL2/S2 or KIR2DL3 (FIG. 1B), the inventors next examined whether there was any influence of cognate-(self-) HLA class I molecules on the KIR expression on the expanded cells. Indeed, expanded NKG2C$^+$NKG2A$^-$ NK cells in CMV-seropositive donors displayed a near clonal expression of KIR specific for self HLA class I molecules (hereafter referred to as self-specific KIR) (FIG. 3A). Remarkably, in some donors such "clones" represented more than 60% of the whole CD56$^{dim}$ NK cell compartment (FIG. 3B). To analyze the overarching impact of such NK cell expansions on the KIR repertoire, donors were stratified based on HCMV serology in addition to their HLA background. CMV seropositive individuals displayed a striking bias for self-specific KIR that was most pronounced in the NKG2C$^+$NKG2A$^-$ NK cell subset (FIG. 3C). Hence, HLA-C1/C1$^+$ donors had high frequencies of NK cells expressing KIR2DL3 as their only inhibitory KIR, whereas HLA-C2/C2$^+$ donors had high frequencies of NK cell expressing KIR2DL1 as their only inhibitory KIR. In contrast, CMV-seronegative donors exhibited essentially random KIR expression patterns without evidence of repertoire skewing regardless of which subset of NK cells that was analyzed (FIG. 3C). Furthermore, independently of the CMV serological status, there was no bias for expression of self-specific KIR in the more immature NKG2$^+$ CD56$^{dim}$ NK cell compartment (FIG. 3C, left panels).

NK Cell Education is Essential for Expansion of NKG2$^+$ NK Cells In Vitro

To delineate the contribution of NK cell expansion to skewing of KIR repertoires, the inventors stratified HCMV-seropositive donors into those with and without evidence of NK cell expansion. This analysis revealed that the bias for expression of self-specific KIR was more pronounced in donors with NK cell expansion, due to an effect of NK cell expansion on the observed KIR repertoire skewing associated with HCMV (FIG. 3D).

It is known from before that NK cell education via self-specific KIR tunes the NK cell responsiveness to target cells, including cytolysis and cytokine production. In contrast, previous studies suggest that NK cell education does not influence NK cell responsiveness to cytokines, as measured by proliferation or cytokine production. However, the inventors made the surprising observation that a majority of the NK cells that proliferated extensively in response to 721.221 cells transfected with HLA-E (221.AEH) in IL-15 expressed NKG2C in combination with a self-specific KIR (FIG. 3E). In contrast, no such polarized expansion of NK cells was seen after stimulation with wild-type 721.221 cells (221.wt). The data thus demonstrate that KIR-mediated education is promoting the expansion of NK cells stimulated via NKG2C.

These results show that expression of self-specific KIR is a necessary requirement for efficient expansion of NKG2C$^+$ NK cells in vitro.

The invention herein enables one to rapidly generate NK cells with a given specificity in vitro. These cells may be used for NK cell-based therapy guided by the HLA class I of the patient.

In the present invention NK cells are selectively expanded in vitro to gain NK cells of a given KIR specificity. This in vitro expansion as well as the use of these specific NK cells in therapy is novel.

The donor is selected based on their KIR ligand status. Thus, the donor is selected to have NK cells of a desired, or selected, KIR specificity. In particular, the donor is selected to have NK cells which express KIR (specifically inhibitory KIR) which are responsive to (namely which bind) ligands (HLA class I molecules) which are different to the ligands (HLA class I molecules) provided by the target cells in the patient to be treated. Thus, there is an at least partial mismatch at HLA class I between the donor NK cells and the target cells in the patient. Generally this means that there is a mismatch at HLA class I between donor and patient. However, as noted above, a situation where the KIR ligands for the NK cells do not match the HLA class I of the target cells may also be obtained when the target cells do not express HLA class I molecules. Accordingly in one embodiment the donor is chosen to be mismatching to the recipient. In other embodiments the donor may match the recipient.

Major KIR ligands are HLA-C1 (ligand for KIR2DL2/3), HLA-C2 (ligand for KIR2DL1), HLA-Bw4 (ligand for KIR3DL1) and HLA-A3/A11 (ligand for KIR3DL2). A nonlimiting list of suitable mismatches is presented in Table 1. Accordingly, in some embodiments, the donor may be at least partially mismatched to the patient at one or more groups of HLA class I alleles, particularly at HLA-C alleles or HLA-B alleles. As discovered by the inventors of the present invention it is essential to have educated NK cells and this must be considered when selecting a donor, therefore HLA-A3/A11 donors are not considered, since KIR3DL2 NK cells are not educated and will therefore not drive an expansion as described in the present invention and can therefore not be used according to the present invention. This does not exclude that KIR3DL2 is co-expressed on the expanded cells and or contribute to the expansion in yet undisclosed ways. Most often, the protocol involves selection of donors that are homozygous for either HLA-C1 or HLA-C2. However it is also possible to generate cells from HLA-C1/C2 donors.

TABLE 1

Mismatches according to the present invention

| Donor's HLA-C group | Recipient's HLA-C group |
|---|---|
| C1/C1 | C2/C2 |
| C1/C2 | C1/C1 or C2/C2 |
| C2/C2 | C1/C1 |

| Donor's HLA-B group | Recipient's HLA-B group |
|---|---|
| Bw4/Bw4 | Bw6/Bw6 |
| Bw6/Bw4 | Bw6/Bw6 |
| Bw6/Bw6 | none |

Once a donor is selected leukocytes are obtained as known in the art. If desired, when the leukocytes are obtained NK cell isolation is performed as known in the art. For example a system for separating NK cells is available from Miltenyi. The cells can also be expanded directly from peripheral blood mononuclear cells (PBMC) obtained as known in the state of the art. In such applications, NK cell isolation can be done at the end of the cultures as known in the art. Thus, in general the method involves separating or isolating leukocytes from the donor, and optionally isolating NK cells therefrom. The method may be performed on isolated NK cells or on a leukocyte cell fraction or preparation containing NK cells. Separation of NK cells is standard and well known in the art and may be performed by negative and/or positive selection for NK cells, for example using cell markers for NK cells, and/or by depleting other (non-NK) cell types from the cell population. Alternatively, if NK cells are not isolated for carrying out the expansion method, they can be isolated or enriched after the expansion step. For example NK cells may be isolated from the expanded cell population using standard techniques as discussed above. Alternatively, T and/or B cells may be depleted from the expanded cell population, again using standard techniques readily available in the art. Generally speaking isolation of or enrichment for NK cells will be necessary when the donor cells are not matched to the patient HLA class I (i.e. where there is an at least partial HLA class I mismatch between donor and recipient).

The expansion step (step (c)) involves contacting the cells with the NKG2C and/or NKG2A stimulator. It will be understood that this step thus involves contacting (or incubating) the cells under conditions which promote or enable cell expansion. Such conditions (namely conditions required for NK cell expansion) are well known in the art and essentially the invention lies in using and modifying such state of the art conditions, by providing a stimulator of the paired NKG2C and NKG2A receptors, to skew the expansion towards educated NKG2C$^+$NKG2$^-$ cells of given KIR specificity. As is well known in the art, additional signals for NK cell expansion may be provided through a multitude of receptors, including but not limited to NKG2D, NKp46, CD2, 2B4, DNAM-1 and CD137, or a combination thereof. The stimuli for such receptors may be provided by appropriate feeder cells or by complexes of the stimulatory molecules or receptor ligands e.g. on beads. As noted above, techniques for this are well established.

Leukocytes (e.g. PBMC) or isolated NK cells are cultured with the NKG2C and/or NKG2A stimulator under the appropriate conditions, as mentioned above. Cytokines may additionally be added, including but not limited to IL-5, IL-15, IL-12, IL-18, IL-2, IL-7, IL-21 or IFN-alpha or a combination with one or more of these cytokines. These cytokines or other agents can be used to stimulate proliferation and/or promote apoptosis. In some embodiments the cells are cultured with IL-15.

The NK cells are expanded in the presence of the stimulator by any suitable technical procedure. The stimulator of NKG2C and/or NKG2A may be any ligand, natural or synthetic, that can bind to and stimulate one or both of these receptors or their constituent monomers. In other words, the stimulator is an agonist of the NKG2C and/or NKG2A receptors. Thus, the stimulator may be a ligand or agonist for CD94, or for NKG2C and/or NKG2. As indicated above, the stimulator is preferably the natural ligand HLA-E. As noted above, HLA-E needs to be provided in a form in which it is able to stimulate the cells, and again this is well understood in the art. Thus the HLA-E may be provided in complex with leader sequence peptides. For example leader sequence peptides can be derived from HLA-A, HLA-B, HLA-C or HLA-G molecules. It is known in the art how to insert a sequence encoding the leader peptide into genetic constructs expressing HLA-E so that the HLA-E is expressed in a complex form capable of binding to and stimulating the NKG2C/NKG2A receptors. Cell lines expressing such constructs are known and available, for example cell line 221AEH used in the Examples below. Such cell lines may be used as feeder cells to provide HLA-E to the donor NK cells.

In other embodiments, HLA-E multimers e.g. tetramers or pentamers, may be used, together with any relevant peptide that provides a signal to CD92/NKG2A and/or CD92/NKG2C. Such multimers may be coated onto to an appropriate solid support e.g. beads, or plastic supports or vessels e.g, plates or bags, to provide the desired combined stimulation/inhibition effects, as described above.

In yet other embodiments the stimulator may be an antibody which binds to one or more of CD94, NKG2C or NKG2A. It will be understood that this will be an agonistic antibody, namely an antibody which is capable of stimulating the receptor. Combinations of such antibodies may be used, for example an antibody which binds to NKG2C may be used together with an antibody that binds to NKG2A. Preferably the antibody is anti-NKG2C, or anti-NKG2C together with anti-NKG2A.

Thus the step of expanding the NK cells may be achieved by methods including but not limited to a) using a feeder cell line engineered by different means to express HLA-E (including but not limited to 721.221.HLA-E or K562-HLA-E, or variants of these cell lines modified to express (or overexpress) agonists stimulating for example IL-15 and/or IL-21 receptors, or ligands for activating receptors such as PVR, CD48 or ICAM-1) or b) plates or bags coated in soluble HLA-E complexes alone or in combination with cytokine receptor complexes or c) plates or bags coated with anti-NKG2C mAbs and/or anti-CD94 and/or anti-NKG2C and/or anti-NKG2A mAbs or d) beads coated with soluble HLA-E complexes and/or anti-CD94 and/or anti-NKG2C and/or anti-NKG2A mAbs. The HLA-E construct used in the embodiments described in a-b uses the generic molecule or a modified construct with improved stability and/or binding to the CD94/NKG2A/C molecules based on changes in the leader sequence peptides. These include but are not limited to HLA molecules coupled to the HLA-A and HLA-G leader and peptide modifications thereof. Leukocyts (PBMC) or isolated NK cells can be cultured under conditions known in the art and as described herein.

The term "antibody" as used herein refers to any type of antibody, or any antibody fragment or derivative. For example, the antibody may be polyclonal or monoclonal. The antibody may be of a single specificity. The antibody may be of any convenient or desired species, class or sub-type. Furthermore, the antibody may be natural, derivatised or synthetic. The term antibody as used herein thus includes all types of antibody molecules and antibody fragments.

More particularly the "antibody" may be:

(a) any of the various classes or subclasses of immunoglobulin e.g. IgG, IgA, IgM, IgD or IgE derived from any animal e.g. any of the animals conventionally used e.g. sheep, rabbits, goats, or mice or egg yolk (b) monoclonal or polyclonal antibodies (c) intact antibodies or fragments of antibodies, monoclonal or polyclonal, the fragments being those which contain the binding region of the antibody e.g. fragments devoid of the Fc portion (e.g. Fab, Fab', F(ab')2, Fv), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains (d) antibodies produced or modified by recombinant DNA or other synthetic techniques, including monoclonal antibodies, fragments of antibodies, humanised antibodies, chimeric antibodies, or synthetically made or altered antibody-like structures. Also included are functional derivatives or "equivalents" of antibodies e.g. single chain antibodies. A single chain antibody may be defined as a genetically engineered molecule containing the variable region of the light chain, the variable region of the heavy chain, linked by a suitable polypeptide linker as a fused single chain molecule. Also included are single chain (Sv) intrabodies.

Methods of making such antibody fragments and synthetic and derivatised antibodies are well known in the art. Also included are antibody fragments containing the complementarity-determining regions (CDRs) or hypervariable regions of the antibodies. These may be defined as the region comprising the amino acid sequences on the light and heavy chains of an antibody which form the three dimensional loop structure that contributes to the formation of the antigen binding site. CDRs may be used to generate CDR-grafted antibodies. As used herein "CDR grafted" defines an antibody having an amino acid sequence in which at least parts of one or more sequences in the light and/or variable domains have been replaced by analogous parts of CDR sequences from an antibody having a different binding specificity for a given antigen. One of skill in the art can readily produce such CDR grafted antibodies using methods well known in the art.

A chimeric antibody may be prepared by combining the variable domain of an antibody of one species with the constant regions of an antibody derived from a different species. The expanded cells can then be infused to patients to be treated e.g. patients with cancer, infectious diseases, immunodeficient patients or patients with autoimmune diseases and since the donors are selected in such way that the transfer of NK cells are performed over HLA barriers this will trigger alloreactivity. The cells can also be infused in HLA-matched settings provided that the relevant HLA class I allele is low or absent. Cells can be infused using any suitable method known in the art or as described herein.

Making the transfer in conjunction with therapeutic mAbs can further enhance the desired cellular specificity. Suitable mAbs include but are not limited to Rituximab (anti-CD20), GA 101 (anti-CD20), mabcampath (anti-CD52), mylotarg, and cetuximab. Genetically modifying the expanded cell product can further enhance the desired specificity. Suitable modifications include but are not limited to expression of chemokine receptors such as CXCR5, CCR5 and CCR2 and chimeric antigen receptors such as CD19 linked to CD3zeta and 41-BB and TcRs specific for tumor antigens including but not limited to CD20.

Another embodiment involves the co-expression of activating KIRs on the expanded NK cells. The inventors have successfully expanded NK cells expressing for example KIR2DL3 (recognizing HLA-C1) together with the activating KIR2DS1 (recognizing HLA-C2). These cells can be generated with the here described invention and display highly potent killing of HLA mismatched HLA-C2/C2 leukemic cells. In one embodiment, the protocol is combined with ligands for the activating KIR (including but not limited to HLA-C2) to further stimulate expansion of such cells.

In one embodiment such NK cells expressing a desired combination of inhibitory and activating KIRs are infused to patients patients with cancer, infectious diseases, immunodeficient patients or patients with autoimmune diseases and since the donors are selected in such way that the transfer of NK cells are performed over HLA barriers this will trigger alloreactivity.

The NK cells obtained by the present method have a customized KIR specificity, based on the selected donor, and the majority of the cells lack the NKG2A inhibitory receptor (NKG2A$^-$NKG2C$^+$). When the in vitro expanded NK cells are infused to a patient they will be highly cytolytic since the cells have a customized KIR specificity, are NKG2C positive, lack the inhibitory receptor NKG2A and are differentiated.

When stimulating NK cells with HLA-E this will generate a proliferation that promotes cells lacking NKG2A and at the same time only educated, potent tumor killing, NK cells will proliferate. This is a new way of expanding effective NK cells.

EXAMPLE 1

In Vitro Expansion of NK Cells

Isolated NK cells obtained from donor are cultured together with IL-15 and the feeder cell line 721.221 cells transfected with a hybrid HLA-E containing the HLA-A2 signal sequence (221.AEH) (Lee et al., 1998). NK cells are cultured at a density of 2-10×10$^6$ cells/ml for 12-14 days in X-vivo 15 (BioWhittaker) supplemented with IL-15 and 5% human AB sera at 5% $CO_2$, 37° C. (35-38° C.).

EXAMPLE 2

The Specificity of the Expanded Cells

Figure 4:
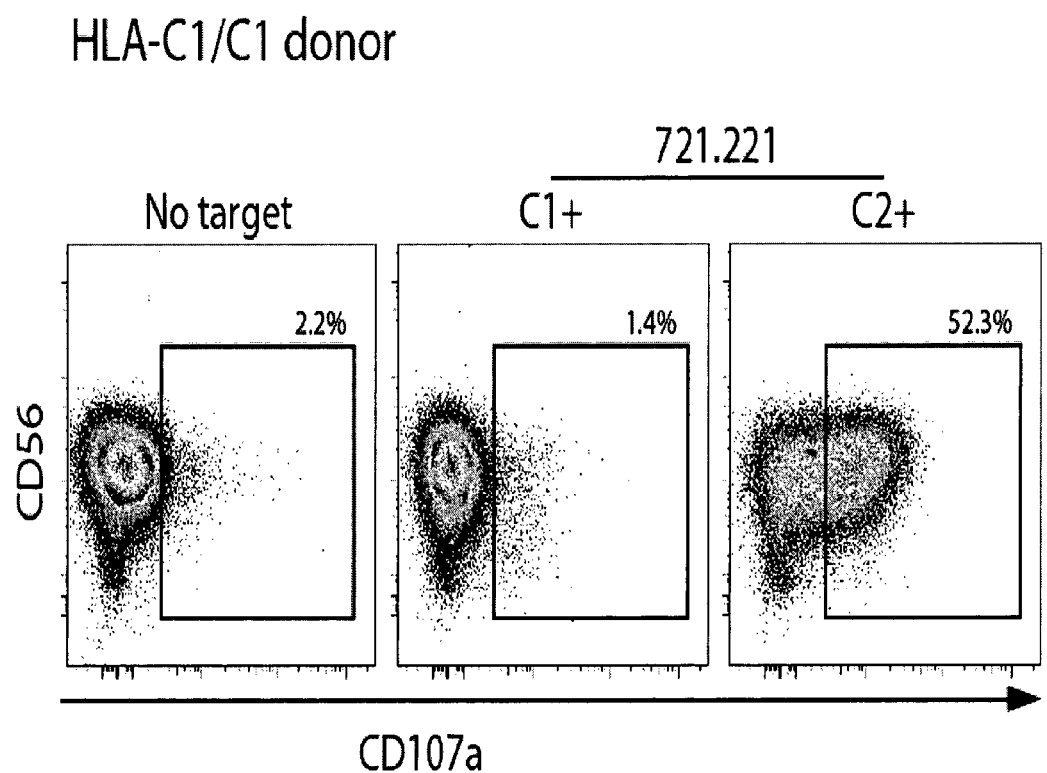

In the example shown in FIG. 4 NK cells were expanded according to example 1 from an HLA-C1/C1 donor and the generated cells were KIR2DL3 single positive. These cells were highly responsive when stimulated by 721.221 cells transfected with HLA-C2 but failed to respond when stimulated by 721.221 cells transfected with the cognate ligand for KIR2DL3, namely HLA-C1. The results reveal the marked specificity of the expanded NK cells.

EXAMPLE 3

Figure 5:
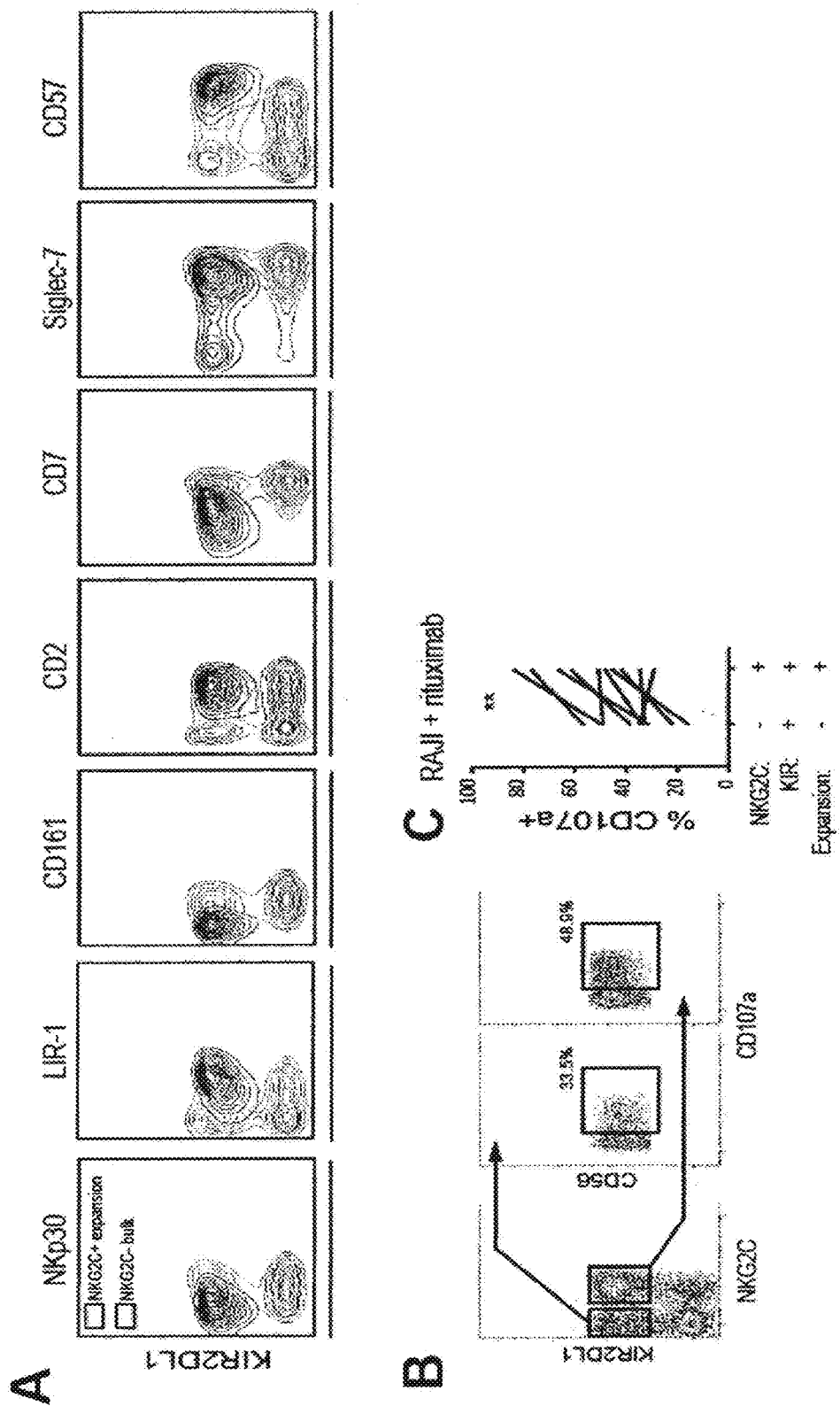
FIG. 5. A differentiated phenotypic and functional fingerprint distinguishes expansions within the NKG2C$^-$ NK cell compartment. (A) Representative staining of the indicated surface molecules on NK cell expansions in the NKG2C$^+$ NK cell subsets. (B-C) Representative staining of CD107a expression in the indicated subset after two hours stimulation with RAH and rituximab. In B-C all comparisons were made with the relevant KIR$^+$ NK cell subset.

Expanded Cells Display a Differentiated Phenotype and Have High Cytolytic Potential Expansion of NK cells according to example 1 is associated with NK cell differentiation, a process during which the cells accumulate effector molecules such as Perforin and Granzyme B, become more responsive to target cell stimulation and highly cytolytic against numerous tumor targets. The cells also become very potent in mediating ADCC against antibody-coated cancer cells (FIGS. 5 and 6).

EXAMPLE 4

Figure 7:
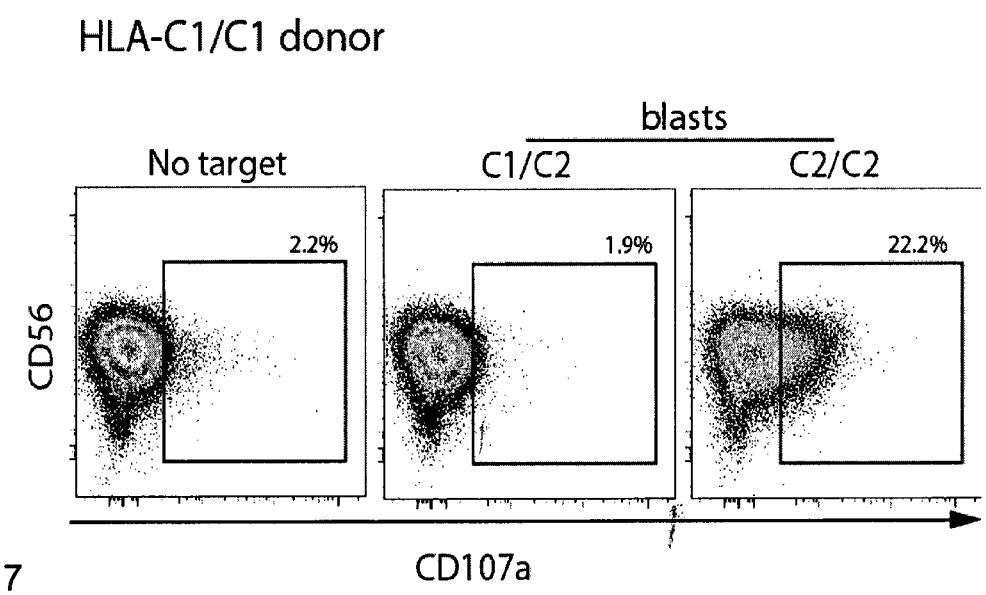
FIG. 7. Specific targeting of HLA-mismatched leukemic blasts.

Expansion of NK Cells under GMP Conditions Yield High Number of Cells that Recognize Mismatched Leukemic Blasts Apheresis of the donor is performed to obtain large number of leukocytes. NK cell isolation is performed in a GMP laboratory using kit and device from Miltenyi. The isolated cells are treated as in example 1. The expanded NKG2C$^+$ KIR2DL3 single positive NK cells display specific killing against mismatched HLA-C2/C2 blasts but not against matched HLA-C1/C1 blasts (FIG. 7).

EXAMPLE 5

Cells expanded according to example 1 are formulated in physiological salt solution supplemented with 5% human serum albumin and filled in a transfer bag for delivery to the clinic immediately upon release. The cells are infused to a patient suffering from acute lymphoid leukemia. The NKG2A$^-$NKG2C$^+$ NK cells with given KIR specificity enhance tumor specificity in this treatment.

EXAMPLE 6

Selective and Controlled Expansion of Educated NK Cells

NK cells were isolated and co-cultured with irradiated 721.221 cells, transfected with HLA-E and the HLA-A leader sequence (221.AEH) in IL-15 for 14 days. Representative FACS plots showing the KIR repertor in NK cells from (A) a C1/C1 donor and (B) a C2/C2 donor at day 0 and day 14 are shown in FIG. 8. (B) shows a summary of the expansion (left panel) and skewing (middle and right panel) in NK cell/221.AEH co-culture experiments from HCMV seropositive donors (n=14). After 14 days of expansion the NK cells display a profoundly skewed KIR repertoire, with on average 90% expression of self-specific KIRs.

This Figure (in particular the middle panel in (B)) illustrates how the protocol generates NK cells with self-specific KIRs. Such cells will be highly specific against HLA-mismatched targets or targets lacking HLA class I.

EXAMPLE 7

Specificity and Efficacy of the Expanded NK Cells

NK cell-mediated killing was assessed in a flow cytometry-based assay by monitoring caspase-3 activity and staining of a live/dead cell marker (DCM) in PHA blasts following co-incubation with NK cells at E:T ratio 5:1 for 4 hours. FIG. 9 shows (A) Representative graphs showing killing of PHA blasts in HLA-C matched and mismatched settings. (B) shows killing of mismatched PHA blasts by expanded NK cells (Day 14) compared to NK cells stimulated with IL-15 over night (Day 0). Expanded NK cells display a more potent in killing of mismatched PHA blasts than short-term activated NK cells.

This Figure illustrates the specificity of the expanded NK cells. Relative to other strategies to expand NK cells, the invented protocol generates cells that display high specificity against matched targets. Due to the unique moulding of the KIR repertoire during culture in combination with the preferential expression of the activating NKG2C rather than the inhibitory NKG2A, the generated cells are highly effective against mismatched targets with high expression of both HLA class I and HLA-E.

EXAMPLE 8

Selectively Expanded NK Cells Efficiency Lyse Primary Blasts from Children with Acute Lymphoblastoid Leukemia The expanded NK cells were tested against primary ALL blasts from 24 children in a FACS-based killing assay at an E:T ratio of 5:1 for 4 hours. FIG. 10 shows (A) Representative FACS plots showing the gating strategy to detect primary ALL blasts after coculture with NK cells. NK cells were stained with CellTrace violet and excluded from the analysis. Markers to identify the ALL blasts were determined according to the minimal residual disease phenotype (NOPHO panel) at the time of diagnosis. (B) shows representative graphs illustrating the killing of subtypes of ALL blasts. (C) shows a summary of the killing of primary ALL blasts with the indicated HLA-C genotype by expanded NK cells expressing KIR2DL1.

This Figure illustrates the efficacy of the expanded NK cells against primary lymphoid leukemia blasts. This is particularly relevant, since ALL cells have been shown to be resistant to NK cells in general and to NK92 cells (the cells sold by CoNKwest) in particular.

EXAMPLE 9

Targeting of High-Risk Myeloid Malignancies

NK cell-mediated killing was assessed in a flow cytometry-based assay by monitoring caspase-3 activity and staining of a live/dead cell marker (DCM) in CD34+ blasts following co-incubation with NK cells at E:T ratio 5:1 for 4 hours. FIG. 11 (A) shows an example of specific killing of CD34+ blasts from patients with myelodysplastic syndrome (MDS) (left) and acute myeloid leukemia (AML). (B) Specific killing of matched and mismatched AML (n=2, one patient was C1/C1 and one C2/C2) and MDS blasts (n=3, all C1/C1).

EXAMPLE 10

Targeting of Malignant Melanoma

Expanded NK cells with two distinct specificities were tested in a standard Cr51-release assay against a range of melanoma cell lines obtained from ATCC (see FIG. 12). The level of killing at the E:T ratios 5:1 and 2.5:1 was in the range of that against the highly NK-sensitive cell line K562.

EXAMPLE 11

Selective Targeting of HLA-C2/C2 Targets by KIR2DL3+KIR2DS1+ NK Cells

NK cell-mediated killing was assessed in a flow cytometry-based assay by monitoring caspase-3 activity and staining of a live/dead cell marker (DCM) in ALL blasts following co-incubation with NK cells at E:T ratio 5:1 for 4 hours. FIG. 13 A) shows an example of killing and specificity of primary ALL blast cells by NK cells expressing KIR2DL3 and KIR2DS1. B) The expanded NK cells were tested against a panel of primary ALL targets with the indicated HLA-C genotype.

The invention claimed is:

1. An in vitro method for expanding NK cells of a given KIR specificity, said method comprising:
   selecting leukocyte cells from a donor, wherein said leukocyte cells comprise educated NK cells of a given KIR specificity, wherein the given KIR specificity is selected with respect to self HLA class I molecules of a patient in need of a therapy; and
   contacting the leukocyte cells in vitro with an HLA-E molecule in complex with a leader sequence from an HLA-A, HLA-B, HLA-C, or HLA-G molecule,
   thereby selectively expanding educated NKG2C+/NKB2A− NK cells of the given KIR specificity within said leukocyte cells to produce an expanded cell population having an increased amount or proportion of NKG2C+/NKG2A− NK cells having said given KIR specificity, when compared to the leukocyte cells prior to expansion.

2. The method of claim 1, wherein said method further comprises isolating or enriching for NK cells of said given KIR specificity from the expanded cell population produced.

3. The method of claim 1, wherein the contacting step further comprises contacting the leukocyte cells with one or more cytokines selected from IL-15, IL-12, IL-18, IL-2, IL-7, IL-21, IFN-alpha, or any combination thereof; and/or one or more ligands for stimulating activating KIR expressed on the NK cells in the leukocyte cells.

4. The method of claim 1, wherein the expanded cell population comprises (i) an increased number and percentage of NKG2C+ NK cells; and/or (ii) a limited or inhibited expansion of NKG2A− NK cells.

5. The method of claim 1, wherein the expanded cell population comprising an increased amount or proportion of NKG2C+/NKG2A− NK cells of said given KIR specificity is produced with a higher efficiency than expanding uneducated NK cells.

6. The method of claim 1, wherein the NK cells of said given KIR specificity in the expanded cell population produced have higher cytolytic potential against HLA-mismatched cells, or cells expressing a low or minimal amount of HLA class I molecules; and are potent in mediating antibody-dependent cellular cytotoxicity (ADCC).

7. The method of claim 1, wherein the leukocyte cells from the donor exhibit an increased amount of educated NK cells expressing KIR specific for donor self HLA class I molecules.

8. The method of claim 1, wherein the donor is cytomegalovirus (CMV) seropositive.

9. The method of claim 1, wherein the leukocyte cells from the donor are homozygous for either HLA-C1, HLA-C2, Bw4 or Bw6, or heterozygous for HLA-C1/C2 or Bw6/Bw4.

10. The method of claim 1, wherein the leukocyte cells from the donor are at least partially mismatched at HLA class I to the patient.

11. The method of claim 10, wherein the leukocyte cells from the donor are partially or fully mismatched to the patient at one or more groups of HLA class I alleles selected from HLA-C1, HLA-C2, Bw4 or Bw6.

12. The method of claim 1, wherein the NK cells of said given KIR specificity are potent in mediating antibody-dependent cellular cytotoxicity (ADCC).

13. The method of claim 1, wherein the HLA-E molecule is (i) exogenous; (ii) expressed by a cell; or (iii) attached to a bead, plate, or bag.

14. The method of claim 1, wherein the leader sequence is derived from HLA-A.

15. The method of claim 1, wherein said KIR specificity is selected from: KIR2DL1, KIR2DL2, KIR2DL3, KIR2DL4, KIR2DL5, KIR3DL1, KIR3DL2, KIR3DL3, KIR2DS1, KIR2DS2, KIR2DS3, KIR2DS4, KIR2DS5, KIR3DS1, or combinations thereof.

* * * * *